US011694813B2

(12) United States Patent
El Katerji et al.

(10) Patent No.: US 11,694,813 B2
(45) Date of Patent: Jul. 4, 2023

(54) LEFT VENTRICULAR VOLUME AND CARDIAC OUTPUT ESTIMATION USING MACHINE LEARNING MODEL

(71) Applicant: Abiomed, Inc., Danvers, MA (US)

(72) Inventors: Ahmad El Katerji, Danvers, MA (US); Qing Tan, Danvers, MA (US); Erik Kroeker, Danvers, MA (US); Rui Wang, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 528 days.

(21) Appl. No.: 16/743,797

(22) Filed: Jan. 15, 2020

(65) Prior Publication Data

US 2020/0222607 A1 Jul. 16, 2020

Related U.S. Application Data

(60) Provisional application No. 62/793,239, filed on Jan. 16, 2019.

(51) Int. Cl.
*A61B 5/02* (2006.01)
*A61B 5/029* (2006.01)
(Continued)

(52) U.S. Cl.
CPC ......... *G16H 50/50* (2018.01); *A61B 5/02007* (2013.01); *A61B 5/029* (2013.01);
(Continued)

(58) Field of Classification Search
CPC ........ A61B 5/02028; A61B 2562/0247; A61B 5/026; A61M 60/538; A61M 2205/3334;
(Continued)

(56) References Cited

U.S. PATENT DOCUMENTS

2014/0114202 A1 4/2014 Hein et al.
2017/0119261 A1 5/2017 Teixeira
(Continued)

FOREIGN PATENT DOCUMENTS

WO 2018134330 A2 7/2018

OTHER PUBLICATIONS

International Search Report for Application No. PCT/US2020/013672 dated Jul. 10, 2020.
(Continued)

*Primary Examiner* — Jon Eric C Morales
(74) *Attorney, Agent, or Firm* — Botos Churchill IP Law LLP

(57) ABSTRACT

Methods and systems are disclosed for creating and using a neural network model to estimate a cardiac parameter of a patient, and using the estimated parameter in providing blood pump support to improve patient cardiac performance and heart health. Particular adaptations include adjusting blood pump parameters and determining whether and how to increase or decrease support, or wean the patient from the blood pump altogether. The model is created based on neural network processing of data from a first patient set and includes measured hemodynamic and pump parameters compared to a cardiac parameter measured in situ, for example the left ventricular volume measured by millar (in animals) or inca (in human) catheter. After development of a model based on the first set of patients, the model is applied to a patient in a second set to estimate the cardiac parameter without use of an additional catheter or direct measurement.

20 Claims, 12 Drawing Sheets

500

502 Operate a Blood Pump within a Patient

504 Measure at Least One Measurable Pump Parameter of the Blood Pump in the Patient to Acquire a Pump Parameter Measurement 506 Measure at Least One Hemodynamic Parameter in the Patient to Acquire a Hemodynamic Parameter Measurement 508 Access a Model of a Relationship Between the at Least One Measurable Pump Parameter, the at Least One Hemodynamic Parameter, and a Cardiac Parameter 510 Using the Model, Estimate a Cardiac Parameter Estimate for the Patient Based on the Pump Parameter Measurement and the Hemodynamic Parameter Measurement

(51) Int. Cl.

| | |
|---|---|
| ***A61B 5/0215*** | (2006.01) |
| ***A61B 5/00*** | (2006.01) |
| ***G16H 50/50*** | (2018.01) |
| ***A61M 60/422*** | (2021.01) |
| ***A61M 60/216*** | (2021.01) |
| ***A61M 60/546*** | (2021.01) |
| ***A61M 60/122*** | (2021.01) |
| ***A61M 60/515*** | (2021.01) |
| ***A61M 60/585*** | (2021.01) |
| ***A61M 60/538*** | (2021.01) |
| ***A61M 60/523*** | (2021.01) |
| ***A61M 60/592*** | (2021.01) |
| ***A61M 60/531*** | (2021.01) |

(52) U.S. Cl.

CPC ........ *A61B 5/0215* (2013.01); *A61B 5/02028* (2013.01); *A61B 5/6852* (2013.01); *A61M 60/122* (2021.01); *A61M 60/216* (2021.01); *A61M 60/422* (2021.01); *A61M 60/515* (2021.01); *A61M 60/523* (2021.01); *A61M 60/531* (2021.01); *A61M 60/538* (2021.01); *A61M 60/546* (2021.01); *A61M 60/585* (2021.01); *A61M 60/592* (2021.01); *A61M 2205/04* (2013.01); *A61M 2205/103* (2013.01); *A61M 2205/3334* (2013.01); *A61M 2205/3365* (2013.01); *A61M 2205/502* (2013.01); *A61M 2206/10* (2013.01)

(58) Field of Classification Search

CPC .. A61M 2205/3344; A61M 2205/3365; A61M 60/13; A61M 60/216; A61M 60/554; A61M 60/531; A61M 60/515; A61M 60/546

See application file for complete search history.

(56) References Cited

U.S. PATENT DOCUMENTS

2018/0078159 A1 3/2018 Edelman et al.
2018/0280598 A1 10/2018 Curran et al.

OTHER PUBLICATIONS

Partial Search Report and Provisional Opinion for Application No. PCT/US2020/013672 dated May 19, 2020.

Search Report and Written Opinion from corresponding Singapore Patent Application No. 11202107369Y dated May 10, 2023 (11 pp.).

LEFT VENTRICULAR VOLUME AND CARDIAC OUTPUT ESTIMATION USING MACHINE LEARNING MODEL

CROSS-REFERENCE TO RELATED APPLICATIONS

This application claims the benefit of priority under 35 U.S.C. § 119(e) from U.S. Provisional Application Ser. No. 62/793,239 filed Jan. 16, 2019, the contents of which are hereby incorporated by reference in their entirety.

BACKGROUND

Cardiovascular diseases are a leading cause of morbidity and mortality, and pose a burden on healthcare around the world. A variety of treatment modalities have been developed for cardiovascular disease, ranging from pharmaceuticals to mechanical devices and finally transplantation. Temporary cardiac support devices, such as ventricular assist devices, provide hemodynamic support, and facilitate heart recovery. Some ventricular assist devices are percutaneously inserted into the heart and can run in parallel with the native heart to supplement cardiac output, such as the IMPELLA® family of devices (Abiomed, Inc., Danvers Mass.).

The amount of support, as measured by the volumetric flow of blood delivered by the pumping device, or the duration of support that each patient needs can vary. It is difficult for clinicians to directly and quantitatively determine how much support a device should deliver or when to terminate use of a cardiac assist device, particularly for patients who recover from intervention or other cardiac care. Thus, clinicians tend to rely on judgments and indirect estimates of cardiac function, such as measuring intracardiac or intravascular pressures using fluid-filled catheters.

While fluid-filled catheters can provide important measurements of cardiac parameters that enable health care professionals to make decisions about a patient's cardiac care and health, the presence of diagnostic equipment in the blood vessels can be risky to the patient and may be less precise than would be desired; in some cases the equipment can interfere with the functionality of the pumping device.

SUMMARY

The methods, systems, and devices described herein enable the creation and use of a model relating blood pump parameters to a cardiac parameter based on a first patient population, which can then be applied to a second patient population to estimate the cardiac parameter without the use of an additional measurement catheter or other diagnostic device. In particular, the methods and systems enable the use of machine learning to develop a model representing the relationship between measured parameters of a blood pump and a cardiac parameter, such as left ventricular volume or cardiac output, for a first patient set. The machine learning algorithm constructs a model of the measured cardiac parameter with regard to one or more measurable parameters of a blood pump based on data from a large number of patients having various characteristics such as sex, weight, disease state, cardiac outcomes, diagnosis, or other characteristics. After the model is developed, which predicts the cardiac parameter measured by a diagnostic device (e.g., a fluid-filled catheter), the model can then be accessed and applied to patients in a second patient set to estimate the cardiac parameter (such as cardiac output) based on pump parameters without use of an additional catheter or other diagnostic device.

In particular, a model is created by tracking blood pump performance parameters such as pump speed, current, flow, and pressure in the vessel where the pump is positioned (such as aortic pressure measured by on-board optical or other pressure sensors on the pump itself), and measuring one or more hemodynamic parameters, such as a left ventricular volume, left ventricular pressure, pulmonary artery pressure, or other cardiac parameter (such as by a pressure sensing catheter) over a time period in a plurality of patients who make up a model training group. The data is collected, stored, and then analyzed using a machine learning algorithm to extract a curve fit for the patient set or for a particular sub-group of patients. For example, a model may be extracted that indicates cardiac output based on pump performance parameters and measured hemodynamic parameters from a population of patients in the patient set. The model may be applicable to all patients in the patient set, or to one or more patients in the patient set, or a model may be extracted that is applicable to a subset of patients in the set that have a particular characteristic. For example, in some embodiments different models may be determined for all patients diagnosed with cardiogenic shock, or myocardial infarction, or may be based on patient demographics such as sex, weight, or risk factors. In another example, the model is applicable to all types of patients regardless of their diagnosis or various demographics.

The model is created by use of neural networking to fit the large amount of stored data to a model. At each time point in the pressure and flow data measured in a particular patient in the patient population, the neural network may use the pressure and the flow data (or pump speed or other parameters) extracted from the blood pump to calculate a cardiac parameter such as left ventricular pressure, and compare the calculated cardiac parameter to the true measurement of the parameter as determined by the catheter. The neural network may include a plurality of cells which communicate with one another to develop a model based on the relationship between the pump parameters (e.g., pump speed, pressure and flow data) and the cardiac parameters. The cells receive the pump performance data (e.g., pump speed, pressure and flow) and hemodynamic parameters as inputs at a first time point and transform the inputs based on model fits. The inputs to the model may be hemodynamic parameters and pump parameters which can be related to the measured cardiac parameter. The neural network may be a stacked neural network, for example a stacked bidirectional recurrent neural network, which communicates over time in hidden states, and develops the model based on multiple activation functions to iteratively develop the model. A cell of the neural network may, for example, transform the inputs based on model fits and then transmit the transformed inputs to a next cell in the stack along with an updated hidden state and cell state. The final model output from the neural network is able to accurately represent cardiac output, or left ventricular volume (or other cardiac function) based on the pump parameters without the use of a catheter.

The model can then be applied to patients who are outside of the training group. In the case of a model which is applicable to patients regardless of demographic or diagnosis, the model may be applied to all patients in a second group not part of the model training group. In another embodiment, a health care provider may input various demographics of a patient and an appropriate model is chosen based on the patient demographics. The model is then applied to the blood pump parameters measured for the patient and an estimated cardiac parameter is extracted. For example, the blood pump speed and aortic pressure measured in a patient can be used with the model to extract an estimated left ventricular pressure or cardiac output. The estimated left ventricular pressure illustrates the patient's cardiac health over time.

The model can be used to provide health care professionals with a continuous or nearly continuous estimate of a cardiac parameter while the pumping device is in the patient, enabling the health care professional to make real-time decisions about the patient's care. For example, the provided estimated cardiac parameter can be used by a health care professional in decisions related to cardiac health, weaning the patient from the pumping device support or increasing support. The cardiac parameter may be a left ventricular volume, cardiac output, cardiac power output, compliance, native flow, stroke volume, volume at diastole or systole, or other relevant cardiac parameter, or any combination of the foregoing. Other hemodynamic or cardiac parameters may be determined using the estimated cardiac parameter and provided to a health care professional as well.

In an aspect, a method of estimating a cardiac parameter for a patient includes operating a blood pump within each patient in a first patient set, the blood pump having at least one measurable pump parameter, measuring at least one hemodynamic parameter and the at least one measurable pump parameter for each patient in the first patient set to acquire a first hemodynamic parameter measurement and a first pump parameter measurement, and building a model of one or more cardiac parameters based on a relationship between the at least one first hemodynamic parameter and the at least one measurable pump parameter for the first patient set. The model may include a neural network with inputs of hemodynamic parameters and pump parameters from multiple patients within the first set. The method further includes operating a second blood pump in a second patient in a second patient set, and applying the model to the second patient by measuring the at least one measurable pump parameter in the second patient to acquire a second pump parameter measurement, measuring the at least one first hemodynamic parameter in the second patient to acquire a second hemodynamic parameter measurement, and estimating a cardiac parameter for the second patient, where the cardiac parameter for the second patient is output by the model based on the second pump parameter measurement and the second hemodynamic parameter measurement. In some implementations, the method further includes determining an estimated cardiac parameter based on the at least one hemodynamic parameter and at least one measurable pump parameter for at least one time point. In some implementations, the method includes inserting into each patient within the first patient set a sensing catheter separate from the blood pump (for example placing the catheter in the left ventricle, or pulmonary artery), and measuring at the sensing catheter a hemodynamic parameter (such as left ventricular end diastolic pressure, or pulmonary capillary wedge pressure). The measured hemodynamic parameter may be used to calculate cardiac output or other cardiac parameter, as a measured parameter. In some implementations, the method further includes comparing the estimated cardiac parameter based on output from the model to the measured cardiac parameter based on an input provided from a reading of the sensing catheter. Ultimately, pump operation can be established and adjusted based on the estimated cardiac parameters from the model, for example by using the estimated cardiac parameters from the model as inputs to a pump controller configured to receive such parameters and adjust the pump output.

In some implementations, the method includes displaying the second pump parameter measurement and the second hemodynamic parameter measurement for the second patient on a display, displaying the estimated cardiac parameter of the second patient on the display, and/or computing a suggested change in a pump speed based on the estimated cardiac parameter in the second patient. In some implementations, the method further includes implementing the suggested change in pump speed.

In some implementations, building a model of a cardiac parameter comprises using a neural network to extract a model from the at least one first hemodynamic parameter and the at least one measurable pump parameter for the first patient set. The model may be extracted from multiple parameters, including multiple hemodynamic parameters and multiple pump parameters, taken from one or multiple patients. The model is stored in a memory and may be onboard or otherwise accessible over a network by a pump controller. The neural network may include a plurality of cells. In some implementations, the plurality of cells are in communication with one another and the cells accept one or more parameters (measured parameters such as pump parameters and hemodynamic parameters, or combinations of pump parameters and hemodynamic parameters) as inputs and transform the one or more parameters based on a model fit. One or more cells may transmit the transformed parameters to a neighboring cell, such as a cell having a hidden state or a cell state. In some implementations, a first cell in the neural network accepts one or more hemodynamic parameters and one or more measurable pump parameters for a first patient set as inputs at a first time point. The first cell in the neural network may receive multiple parameters or combinations of parameters, such as multiple hemodynamic parameters and multiple pump parameters. In some implementations, the first cell transforms at least one first hemodynamic parameter and at least one measurable pump parameter based on one or more model fits before transmitting the transformed hemodynamic parameter and measurable pump parameter to a second cell in the neural network. In some implementations, the first cell updates a hidden state and cell state for a first time point. In some implementations, the first cell receives at least one first hemodynamic parameter and at least one measurable parameter for a second time point and updates the hidden state and cell state for the second time point. In some implementations, the first patient set is formed of a single patient.

In an aspect, a method of estimating a cardiac parameter for a patient based on a model includes operating a blood pump in a patient, measuring at least one measurable pump parameter of the blood pump in the patient to acquire a pump parameter measurement, measuring at least one hemodynamic parameter in the patient to acquire a hemodynamic parameter measurement, and accessing from a database a model of a relationship between the at least one measurable pump parameter, the at least one hemodynamic parameter, and a cardiac parameter. The method further includes estimating a cardiac parameter estimate for the patient, where the cardiac parameter estimate for the patient is output by the model based on the pump parameter measurement and the hemodynamic parameter measurement.

In some implementations, the methods and systems access a model by determining a selected model from a plurality of available models. In some implementations, the selected model is determined based on information associated with the patient. In some implementations, the method includes choosing a model formed by a neural network including a plurality of cells. In some implementations, the neural network is a recurrent bi-directional neural network. In some implementations, the neural network includes a plurality of cells. In some implementations, the plurality of cells are in communication with one another and the cells accept one or more measured parameters as inputs, transform the one or more measured parameters based on a model fit, and transmit the transformed parameters to a neighboring cell with a hidden state or a cell state. In some implementations, the method includes determining a recommended change in the operation of the blood pump based on the estimated cardiac parameter.

In an aspect, a method for developing an estimate of a cardiac parameter in a patient includes measuring one or more parameters derived from operation of a medical device and measuring a cardiac parameter in a first patient population, developing a model of the cardiac parameter based on the one or more parameters derived from operation of the medical device and the cardiac parameter in the first patient population, and applying the model to a patient in a second patient population to estimate the cardiac parameter for the patient.

In some implementations, the method also includes labeling the model according to common characteristics of one or more patients in the first patient population, and/or determining, based on the labeling of the model, whether the model is applicable to the patient in the second patient population by comparing characteristics of the patient in the second patient population with the characteristics of the one or more patients in the first patient population. In some implementation, the method also includes utilizing a machine learning algorithm to develop a model of the cardiac parameter based on the one or more parameters derived from operation of the medical device and the measured cardiac parameter in the first patient population. In some implementations, a neural network is utilized to develop the model. In some implementations, the neural network includes a plurality of cells. In some implementations, the plurality of cells are in communication with one another and the cells accept one or more measured parameters as inputs, transform the one or more measured parameters based on a model fit, and transmit the transformed parameters to a neighboring cell with a hidden state or a cell state.

In some implementations, applying the model to the patient in the second patient population includes operating the medical device in the patient in the second patient population, measuring, in the patient in the second patient population, the one or more parameters derived from operation of the medical device, inputting the measured one or more parameters derived from operation of the medical device into the model of the cardiac parameter, and estimating, based on the model, an estimated cardiac parameter of the patient in the second patient population.

In an aspect, a system for estimating a cardiac parameter of a patient based on a pre-determined model (such as a model formed by any of the techniques disclosed herein) includes a blood pump and a controller. The blood pump includes a drivable rotor designed to be driven at one or more pump speeds, and a sensor able to measure a hemodynamic parameter. The controller includes a memory which receives a hemodynamic parameter measurement from the sensor and records the hemodynamic parameter measurement, the memory also storing (or accessing from a network) a pre-determined model of a cardiac parameter based on the hemodynamic parameter and a pump speed of the one or more pump speeds (or current, flow, or other pump parameters). The controller also includes a driver designed to drive the rotor and to transmit a pump speed of the driven blood pump rotor (or one or more other pump parameters) to the memory to be recorded, and a display which displays one or more parameters recorded in the memory. The memory uses the pre-determined model and the hemodynamic parameter measurement and pump parameters (e.g., pump speed) to determine an associated cardiac parameter, and transmits the determined cardiac parameter to the display.

In some implementations, the memory stores a plurality of pre-determined models of the cardiac parameter based on the hemodynamic parameters and the pump parameters (e.g., the pump speed, motor current). In some implementations, the controller selects one pre-determined model from the plurality of stored pre-determined models based on one of the hemodynamic parameters or the pump parameters (e.g., pump speed, motor current). In some implementations, the controller selects one pre-determined model from the plurality of stored pre-determined models based on an input to the display. In some implementations, the plurality of pre-determined models are formed by a neural network including a plurality of cells. In some implementations, the neural network is a recurrent bi-directional neural network. In some implementations, the neural network includes a plurality of cells. In some implementations, the plurality of cells are in communication with one another and the cells accept one or more measured parameters as inputs, transform the one or more measured parameters based on a model fit, and transmit the transformed parameters to a neighboring cell with a hidden state or a cell state.

In some implementations, the memory is wirelessly connected to a database containing a plurality of pre-determined models of the cardiac parameter based on the hemodynamic parameter and the pump speed. In some implementations, the controller selects one pre-determined model from the database and retrieve the selected one pre-determined model for storage in the memory. In some implementations, the plurality of pre-determined models are formed by a neural network including a plurality of cells. In some implementations, the neural network is a recurrent bi-directional neural network.

In some implementations, the controller determines a recommended change to the pump speed based on the determined cardiac parameter. In some implementations, the controller generates for display on the display the recommended change to the pump speed. In some implementations, the controller implements for display on the display the recommended change to the pump speed. In some implementations, the sensor measures the aortic pressure. In some implementations, the cardiac parameter is a left ventricular volume. In some implementations, the cardiac parameter is cardiac power, cardiac power output, or another cardiac parameter.

In an aspect, a method of estimating a cardiac parameter for a patient using a database includes operating a blood pump in a first patient, measuring at least one measurable pump parameter of the blood pump in the first patient to acquire a pump parameter measurement, measuring at least one hemodynamic parameter in the first patient to acquire a hemodynamic parameter measurement, and accessing a database comprising patient data for patients other than the first patient, where the patient data includes at least one of a measurable pump parameter, a hemodynamic parameter, and a cardiac parameter. The method further includes using the pump parameter measurement in the first patient, hemodynamic parameter measurement in the first patient, and stored patient data from the database, to estimate a cardiac parameter for the first patient.

In some embodiments, a blood pump is operated in a first patient, and measurable inputs from the first patient are used in combination with a database comprising patient data from patients other than the first patient to estimate a cardiac parameter for the first patient. For example, the database can include cardiac power outputs for a range of patients, along with other measured data. The database includes data from a range of patients having different characteristics (e.g. age, sex, weight, height, etc.). In one example, the database includes data from a range of patients having different medical conditions. The database can be periodically updated to include new data. In some implementations, the database includes models of a relationship between hemodynamic parameters, pump parameters, and cardiac parameters. In some implementations, the models are derived from use of a neural network on patient data. In some implementations, the neural network from which the models are derived includes a plurality of cells. In some implementations, the plurality of cells are in communication with one another and the cells accept one or more measured parameters as inputs, transform the one or more measured parameters based on a model fit, and transmit the transformed parameters to a neighboring cell with a hidden state or a cell state.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the methods and systems described herein, certain illustrative embodiments will be described. Although the embodiments and features described herein are specifically described for use in connection with blood pump devices, it will be understood that all the components and other features outlined below may be combined with one another in any suitable manner and may be adapted and applied to other types of cardiac and medical therapies.

In some embodiments, a blood pump is operated in a first patient, and measurable inputs from the first patient are used in combination with a database comprising patient data from patients other than the first patient to estimate a cardiac parameter for the first patient. For example, the database can include cardiac power outputs for a range of patients, along with other measured data. The database includes data from a range of patients having different characteristics (e.g. age, sex, weight, height, etc.). In one example, the database includes data from a range of patients having different medical conditions. The database can be periodically updated to include new data.

Figure 1:
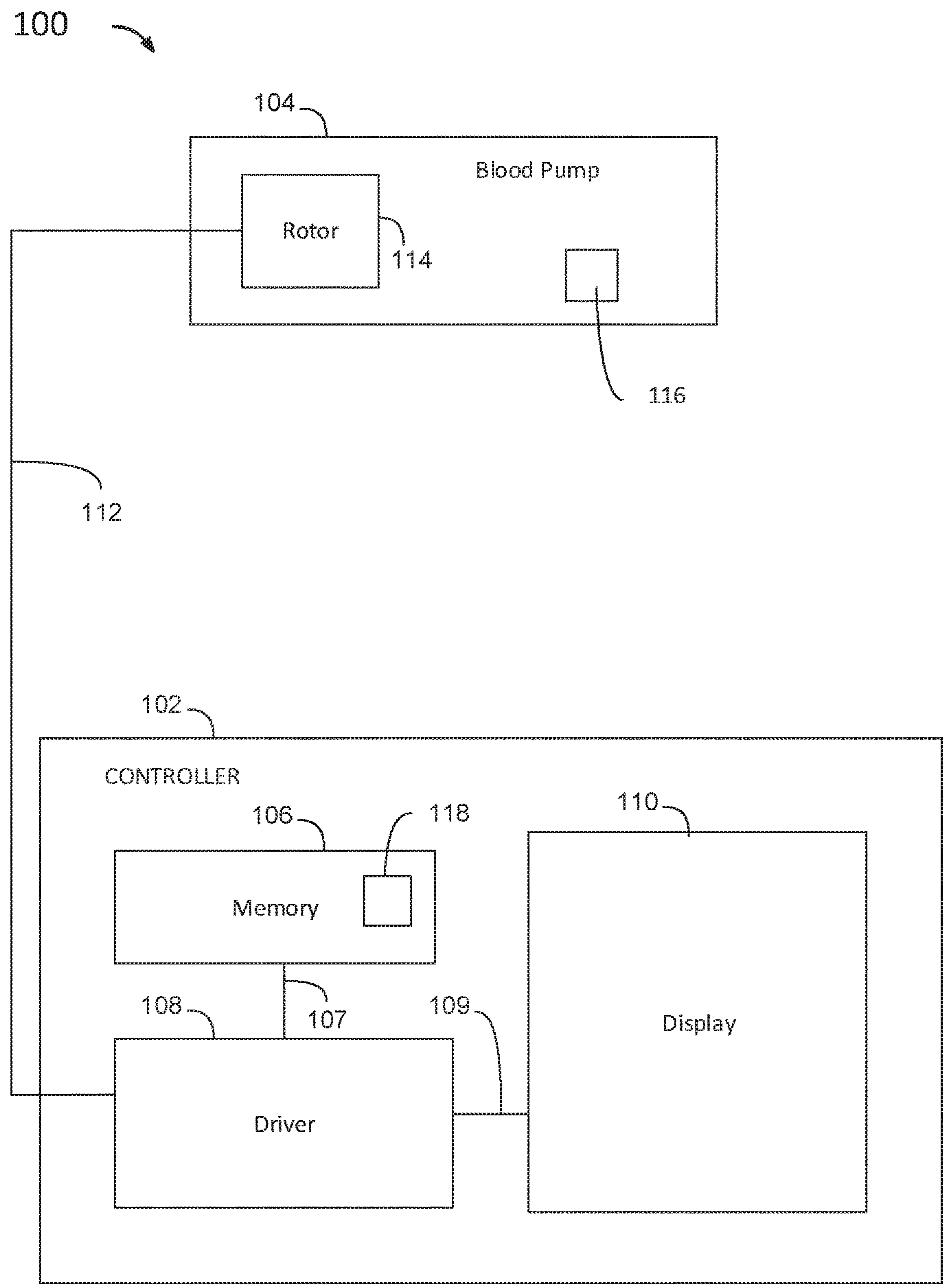
FIG. 1 shows a block diagram of a system for estimating a cardiac parameter of a patient based on a pre-determined model.

FIG. 1 shows a block diagram of a system 100 for estimating a cardiac parameter of a patient based on a pre-determined model. The system 100 includes a controller 102 and a blood pump 104. The controller includes a memory 106 having a pre-determined model 118, driver 108, and display 110. The blood pump 104 includes a rotor 114 and a sensor 116. The controller 102 is communicatively coupled to the blood pump 104 by wire 112, which may be an electrical wire and/or a mechanical drive shaft. The driver 108 within controller 102 controls the blood pump 104 including the speed of operation of the rotor 114. The driver 108 is communicatively coupled to memory 106 by channel 107 and is also communicatively coupled to the display 110 by channel 109. The sensor 116 of the blood pump 104 may be coupled to the controller 102 by wire 112, or may be wirelessly coupled to the controller 102.

The blood pump 104 is operated in the vasculature of a patient to provide cardiovascular support by pumping blood in the patient's heart or vasculature. The speed of rotation of the rotor 114 controls a rate of flow of the blood through the blood pump 104. The sensor 116 is located on the blood pump 104 such that the sensor 116 can measure a hemodynamic parameter of the patient while the blood pump 104 is in place within the patient's vasculature. The sensor 116 transmits the measured hemodynamic parameter to the controller 102 wirelessly or via wire 112. In some implementations, the sensor 116 is an on-board optical sensor or a pressure sensor located on the blood pump 104. In some implementations, the sensor 116 measures an aortic pressure. In some implementations, the sensor 116 measures other hemodynamic parameters.

The controller 102 controls the speed of the rotor 114 by altering the power supplied to the blood pump 104. The driver 108 also measures the load on the rotor 114 by measuring the current supplied to the rotor 114 to maintain a particular rotor speed. The driver 108 stores the measured pump parameters in the memory 106. The driver 108 receives the measured hemodynamic parameter from the sensor 116 and stores these in the memory 106 as well. The driver 108 may also include processing hardware or software (not shown) to enable the hemodynamic parameter and pump parameters to be processed, such as averaged or used to calculate other cardiac parameters in the controller 102. The controller 102 tracks the blood pump parameters such as pump speed, current, flow and pressure in the vessel based on the performance of the blood pump and the hemodynamic parameter measured by the sensor 116. The driver 108 transmits the hemodynamic parameters, pump parameters, or other measured or calculated parameters to the display 110.

The memory 106 includes pre-determined model 118 relating pump parameters to one or more hemodynamic parameters. The creation of such a model is described below. The memory 106 and/or the driver 108 uses the measured pump and hemodynamic parameters with the stored pre-determined model 118 to estimate a particular cardiac parameter based on the measured pump parameters. The cardiac parameter may be a left ventricular volume, cardiac output, cardiac power output, compliance, native flow, stroke volume, volume at diastole or systole, or other relevant cardiac parameter, or any combination of the foregoing. No additional catheters or diagnostic devices may be required to measure the cardiac parameter because the model provides the estimated cardiac parameter based on the model built from other patient data from a first patient set. In some implementations, the memory 106 includes more than one pre-determined model 118, and a particular pre-determined model 118 is selected based on one or more of the measured pump parameters and hemodynamic parameters. In some implementations, a particular pre-determined model 118 is selected from multiple stored models by an input from a healthcare professional. In some implementations, the memory 107 stores a database or is linked to a database from which the pre-determined model is selected.

In some implementations, the driver 108 displays the estimated cardiac parameter on the display 110. In some implementations, the controller 102 uses the estimated cardiac parameter to determine a recommended course of action with regard to increased or decreased support by the blood pump 104. For example, the controller 102 may display on the display 110 recommended changes in the operation of the blood pump 104 based on the measured hemodynamic and pump parameters and the estimated cardiac parameters. In particular, the controller 102 can determine the recommended course of action based on a comparison of the estimated cardiac parameter with previous estimated cardiac parameters for the patient. In some embodiments, the controller 102 may make a change to the support provided by the blood pump 104 based on the proposed course of action. In some embodiments, the controller 102 presents options to a health professional via the display 110 and allow the health professional to select an option to control or change the blood pump 104 operation.

In some implementations, the hemodynamic parameters and pump parameters or other data stored in the memory 106 can be extracted from the memory 106 for use with data from other patients to use in the creation of an algorithm relating blood pump parameters to one or more cardiac parameters. The extracted data may be combined with other health data such as sex, weight, disease state, cardiac outcomes, diagnosis, or other characteristics, and used to create an algorithm based on machine learning or a neural network. In some implementations, the controller 102 is coupled to a database which stores the data from which the pre-determined model is derived, and the controller 102 uploads data to update the database.

Figure 2:
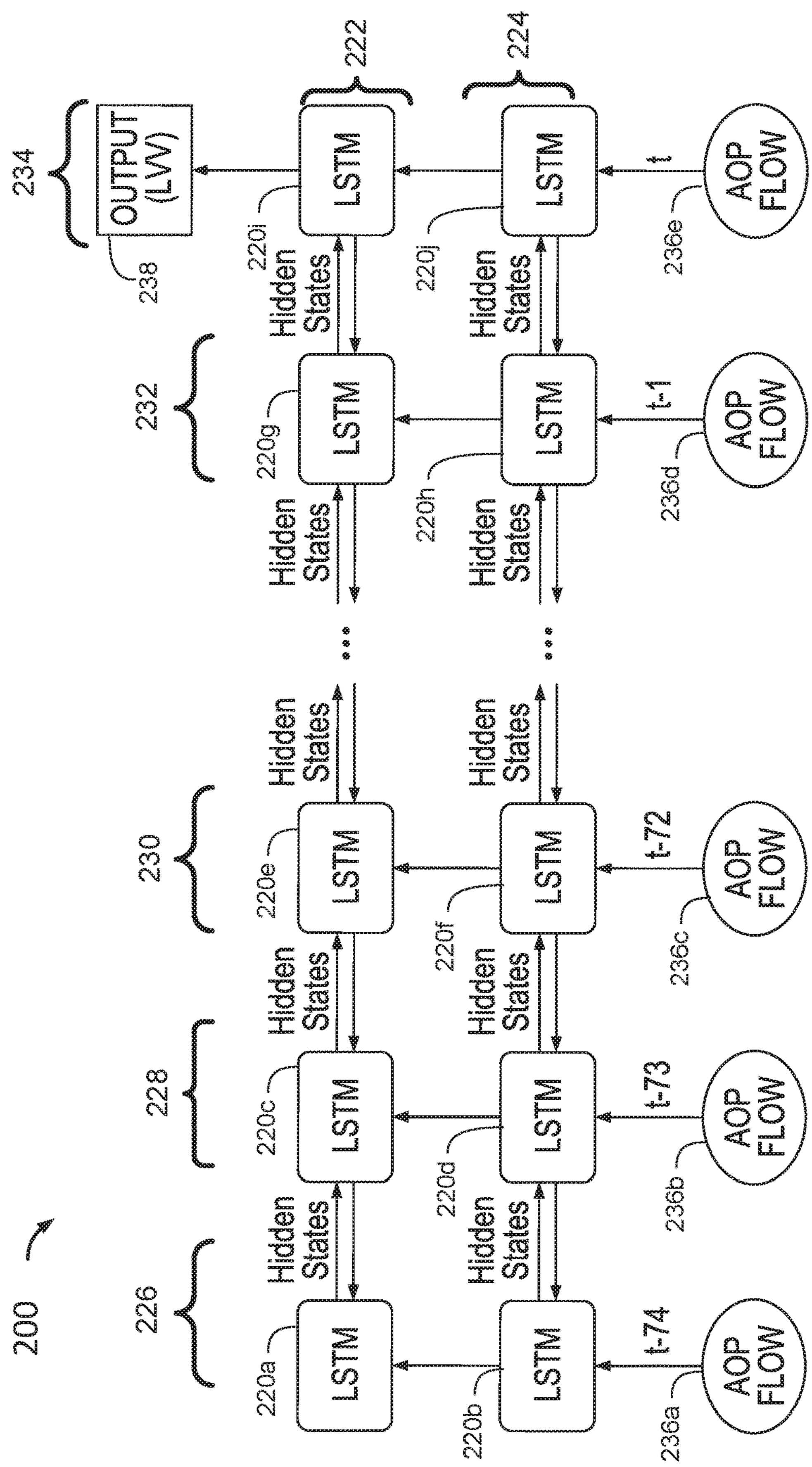
FIG. 2 shows a block diagram of a stacked bidirectional recurrent neural network.

FIG. 2 shows a block diagram of an exemplary stacked bidirectional recurrent neural network 200, which can be used for creation of a model, such as the pre-determined model 118 that can be used in the blood pump system 100 of FIG. 1 to interpret and estimate cardiac parameters from pump parameters measured in a patient. The neural network 200 is used to fit the large amount of data from a training data set including measured parameters from a first patient set. The exemplary neural network can be implemented in creating a model relating blood pump parameters to cardiac parameters, as described above in FIG. 1. The exemplary neural network 200 is a stacked bi-directional recurrent neural network, though other neural network models are also available that are applicable to the creation of the model described herein. The neural network 200 communicates over time in hidden states, and develops the model based on multiple activation functions to iteratively develop the model, as will be described in fuller detail below. The model created using the neural network can then be stored in a controller memory, for example in memory 106 of FIG. 1, and used to estimate cardiac parameters in a patient in which a blood pump is being operated. In this exemplary neural network 200, processing cells 220*a-j* (labeled "LSTM" for long short-term memory) are organized in a grid, having rows 222 and 224 and columns 226-234. The processing cells 220*a-j* communicate between each other along the rows 222 and 224 and columns 226-234. There are multiple levels or rows 222 and 224 stacked between inputs and output, and multiple columns 226-234.

The lowest row 224 is an input row, with inputs 236*a-e* of aortic pressure (AOP) and pump flow (Flow). The highest row 222 is an output row, outputting the estimated output parameter 238, for example left ventricular volume (LVV). The number of rows between the input row 224 and the output row 226 are indicative of model depth or sophistication. For example, the model can be bi-directionally stacked as neural network 200 is in FIG. 2. Alternatively, the model can have three, four, five or more levels of cells stacked between the input row 224 and the output row 222. Each estimation by the neural network 200 is based on a number of states at different sampling times, represented by the number of columns 226-234 in the exemplary neural network 200. For neural network 200, at time t, the neural network 200 receives inputs 236*e* of AOP and flow, and uses information from the neural network 200 for a number of previous states, e.g. 75 states shown as t-74 for inputs 236*a* in column 226 through t-1 for inputs 236*d* in column 232. The neural network 200 computes the estimated cardiac parameter (the output 238) based on a group of at least 25 previous sampling instances. In some implementations, the neural network computes the estimated cardiac parameter (the output 238) based on a group of at least 50, or at least 75 or more previous sampling instances. At each time point in the aortic pressure and flow data measured in a particular patient in the patient population, the neural network may use the pressure and the flow data extracted from the blood pump to calculate a cardiac parameter such as left ventricular pressure, and compare the estimated cardiac parameter to the true measurement of the parameter as determined by the catheter. In some implementations, the cardiac parameter is a left ventricular volume, cardiac output, cardiac power output, compliance, native flow, stroke volume, volume at diastole or systole, or other relevant cardiac parameter, or any combination of the foregoing.

In particular, within each cell of the neural network 200, the neural network 200 generates so-called hidden states and shares these hidden states across different cells. By utilizing the stacked neural network system, it is possible to extract complex relationships between the input data 236*a-e* in order to produce an accurate estimation of an output parameter 238.

The neural network 200 may be used in a machine learning algorithm which constructs a model of a measured cardiac parameter (for example, aortic pressure) with regard to one or more measurable parameters (such as pump speed or flow) of a blood pump (such as blood pump 104 in FIG. 1) based on data from a large number of patients having various characteristics such as sex, weight, disease state, cardiac outcomes, diagnosis, or other characteristics. The patient data is input into the machine learning algorithm to develop a model based on relationships that the algorithm determines between the various pieces of input data. The final model is able to represent an accurate left ventricular volume or cardiac output (or other cardiac function) curve based on the pump parameters without the use of a catheter, and as described above, may be a global model of all physiological conditions equipped to handle any case in a patient population. After the model is developed, which predicts the cardiac parameter measured by a diagnostic device (e.g., a fluid-filled catheter or other internal sensor), the model can then be applied to patients in a second patient set outside of the training group, to estimate the cardiac parameter based on pump parameters without use of an additional catheter or other diagnostic device.

Figure 3:
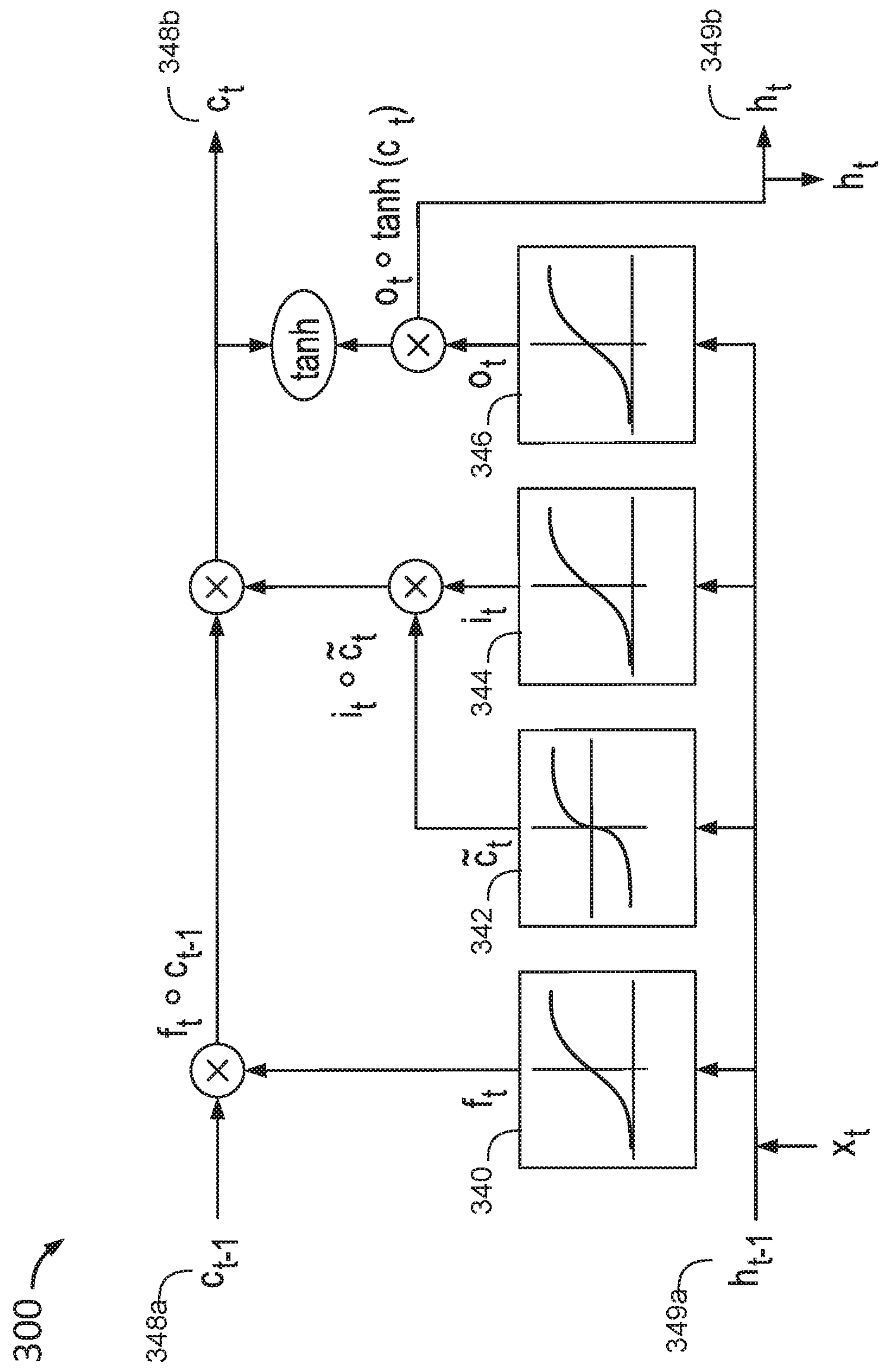
FIG. 3 shows a block diagram of a Long Short-Term Memory Cell of the stacked bidirectional recurrent neural network of FIG. 2.

FIG. 3 shows a block diagram of a Long Short-Term Memory Cell of the stacked bidirectional neural network of FIG. 2. For example, the cells 220*a-j* of the neural network 200 of FIG. 2 can be long short-term memory cells. Alternatively, the cells 220*a-j* of the neural network 200 can be other types of cells. Similarly, the neural network 200 itself can be a neural network such as shown in the example of FIG. 2, or another type of neural network such as fully recurrent, Elman network, Hopfield network, Echo state network, hierarchical, etc. In the example of FIG. 2, the neural network cells are long short-term memory cells. FIG. 3 shows a single long short-term memory cell 300. As shown in FIG. 3, long short-term memory cell 300 has four activation functions, represented by four boxes and their associated functions including first function "$f_t$" 340, second function "$\tilde{c}_t$" 342, third function "$i_t$" 344 and fourth function "$o_t$" 346, respectively. First function "$f_t$" 340 is a sigmoidal function producing a gating variable, second function "$\tilde{c}_t$" 342 is a hyperbolic tangent function producing a candidate state of the memory cell, third function "$i_t$" 344 is a sigmoidal function producing a gating variable and fourth function "$o_t$" 346 is a sigmoidal function producing a gating variable. While the first function "$f_t$" 340, second function "$\tilde{c}_t$" 342, third function "$i_t$" 344 and fourth function "$o_t$" 346 are examples, and other functions can be used in processing information in a cell 300, the exemplary first function "$f_t$" 340, second function "$\tilde{c}_t$" 342, third function "$i_t$" 344 and fourth function "$o_t$" 346 are defined below:

$$f_t=\sigma(W_f[h_{t-1},x_t]+b_t)$$

$$i_t=\sigma(W_i[h_{t-1},x_t]+b_i)$$

$$o_t=\sigma(W_o[h_{t-1},x_t]+b_o)$$

$$\tilde{c}_t=\tan h(W_c[h_{t-1},x_t]+b_c)$$

The cell 300 receives a cell state 348*a* from previous cells ("$c_{t-1}$"), and processes this cell state 348*a* through the first function ("$f_t$") 340 which indicates what elements the cell 300 should no longer take into account, the second function "$\tilde{c}_t$" 342 which indicates what information the cell 300 should extract, the third function "$i_t$" 344 which indicates what information the cell should update, and a fourth function "$o_t$" 346 or summary gate which provides an output used to update the candidate cell. The updated cell state 348*b* is passed to neighboring cells in the neural network. In this example, the cell state is defined by the below equation:

$$c_t=f_t \circ c_{t-1}+i_t \circ \tilde{c}_t$$

The cell 300 receives a hidden state 349*a* from previous cells ("$h_{t-1}$"), and processes this hidden state 349*a*. The hidden state 349*a* is used as an input to the first function ("$f_t$") 340 which indicates what elements the cell 300 should no longer take into account, the second function "$\tilde{c}_t$" 342 which indicates what information the cell 300 should extract, the third function "$i_t$" 344 which indicates what information the cell should update, and a fourth function "$o_t$" 346 or summary gate which provides an output used to update the candidate cell. The updated hidden state 349*b* is passed to neighboring cells in the neural network. As illustrated, the updated hidden state 349*b* is passed to cells which neighbor the cell 300 in the same row or in the same column. In this example, the hidden state is defined by the below equation:

$$h_t=o_t \circ \tan h(c_t)$$

The activation functions or gates can correspond to a range of functions, including sigmoid, hyperbolic tangent, sigmoid, or any combination of these or other functions. The processing of inputs through the various functions of the cell 300 enables a neural network comprising many such cells to access complex relationships amongst data inputs to produce an algorithm that can be applied to other data to predict an outcome.

Figure 4:
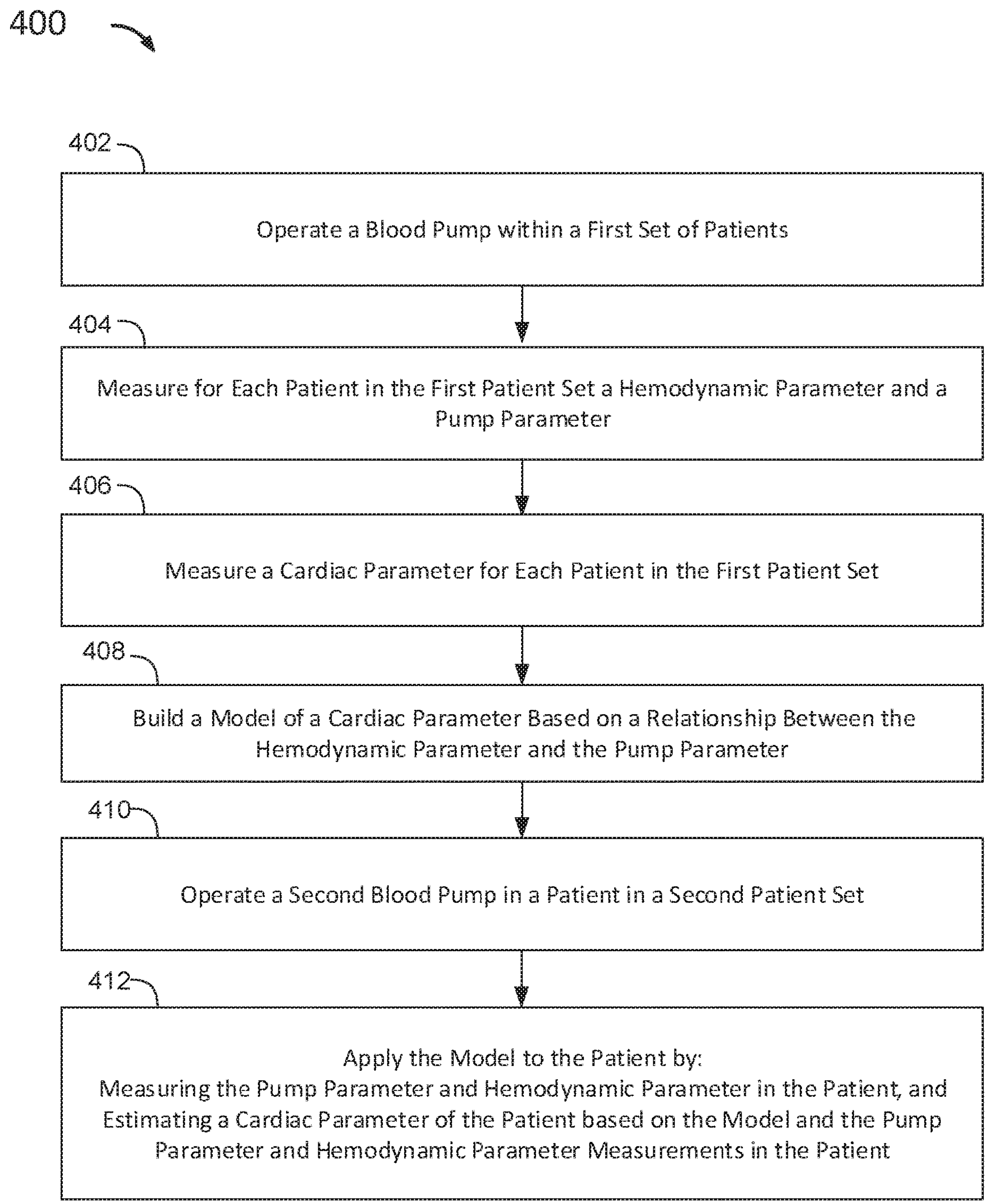
FIG. 4 shows a method of developing and using a model for estimating a cardiac parameter for a patient.

FIG. 4 shows a method 400 of developing and using a model for estimating a cardiac parameter for a patient based on blood pump parameters (for example blood pump 104 in FIG. 1). The method 400 includes step 402 in which a blood pump is operated within a first set of patients. In some implementations, another intravascular medical device such as a balloon pump, centrifugal pump such as an ECMO, pulsatile pump, roller pump or other ventricular assist devices may be used in a similar fashion, rather than a blood pump. At step 404, for each patient in the first set of patients, a hemodynamic parameter and a pump parameter are measured. More than one hemodynamic and/or pump parameter may be measured for each patient in the first set of patients. In some implementations, the hemodynamic and pump parameters measured for each patient are one or more of pump speed, current, flow, and pressure in the vessel, and the measurements are based on the performance of the blood pump. In some implementations, an aortic pressure is measured as the hemodynamic parameter. The hemodynamic parameter is measured by a measurement catheter such as a fluid-filled catheter, inca catheter, millar catheter (for animals), or by another diagnostic device.

In some implementations, one or more of pump speed, flow rate, pump pressure are measured as the pump parameter. The pump parameter is measured by the blood pump controller based on the current supplied to the pump, load on the pump or other characteristic of the blood pump operation. At step 406, the cardiac parameter is measured for each patient in the first patient set. In some implementations, the cardiac parameter is a left ventricular volume, cardiac output, cardiac power output, compliance, native flow, stroke volume, volume at diastole or systole, or other relevant cardiac parameter, or any combination of the foregoing. The cardiac parameter, and hemodynamic and pump parameters, may be measured over a period of time for each of the patient's in the first patient group, which is the model training group.

At step 408, the hemodynamic parameter and pump parameter are used to build a model of a cardiac parameter based on a relationship between the hemodynamic and pump parameter. The data from each of the patients in the first patient set is collected and stored, and then analyzed using a machine learning algorithm to extract a curve fit for the patient set in its entirety, or for particular patient sub-groups. For example, a model may be extracted which is applicable to one or more patients in the patient set, or a model may be extracted that is applicable to a subset of patients in the set that have a particular characteristic. For example, in some embodiments different models may be determined for all patients diagnosed with cardiogenic shock, myocardial infarction, or based on patient demographics such as sex, weight, or risk factors. In another example, the model is applicable to all types of patients regardless of their diagnosis or various demographics.

The model may be built using machine learning or neural networks, such as described above in FIGS. 2 and 3, or any other available machine learning setup. Neural networking can be used to fit the large amount of stored data to a model. Once built, the model may be stored in a controller of the blood pump (for example in memory 106 of FIG. 1), or may be hosted in a server or processor coupled to the blood pump controller or another processor which receives the measured parameters from a blood pump controller.

At step 410, a blood pump is operated in a patient in a second patient set to provide cardiac support. At step 412, the model produced in step 406 is applied to the patient in the second patient set by measuring the pump parameter and hemodynamic parameter in the patient, and estimating the cardiac parameter of the patient based on the model and the pump and hemodynamic parameters measured in the patient in the second set. In this way, an estimated cardiac parameter can be determined for the patient in the second patient set based on the model and without the use of additional catheters or diagnostic tools.

In the case of a model which is applicable to patients regardless of demographic or diagnosis, the model may be applied to all patients in a second group not part of the model training group. In another embodiment, a health care provider may input various demographics of a patient and an appropriate model is chosen based on the patient demographics. The model is then applied to the blood pump parameters measured for the patient and an estimated cardiac parameter is extracted. For example, the blood pump speed and aortic pressure measured in a patient can be used with the model to extract an estimated cardiac parameter such as a left ventricular volume, cardiac output, cardiac power output, compliance, native flow, stroke volume, volume at diastole or systole, or other relevant cardiac parameter, or any combination of the foregoing.

Figure 5:
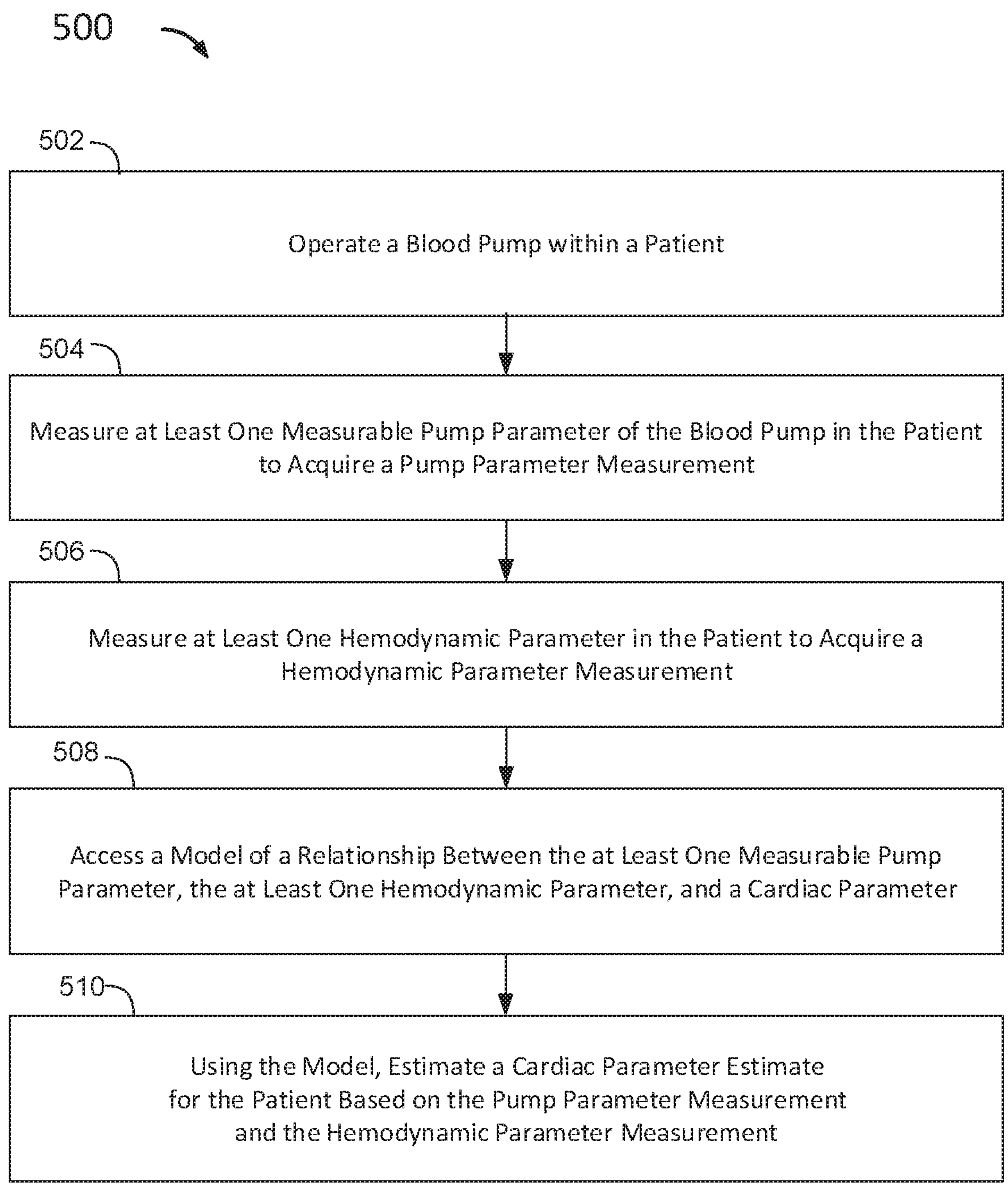
FIG. 5 shows a method of using a model to estimate a cardiac parameter for a patient.

FIG. 5 shows a method 500 of using a model built from data of a first patient set to estimate a cardiac parameter for a patient in a second patient set. At step 502, a blood pump is operated within the vasculature of the patient in the second patient set. At step 504, at least one measurable pump parameter of the blood pump is measured in the patient to acquire a pump parameter measurement. In some implementations, the pump parameter may be a pump speed, flow rate through the pump, or pressure within the pump, and can be measured based on a current supplied to the pump, load on the pump or other characteristic of the blood pump operation. The pump parameter can be measured at the controller of the blood pump (for example, controller 102 in FIG. 1) or at the blood pump itself. At step 506, at least one hemodynamic parameter is measured in the patient to acquire a hemodynamic parameter measurement. In some implementations, the hemodynamic parameter is an aortic pressure. The hemodynamic parameter can be measured by a sensor placed on the blood pump, or on a catheter coupled to the blood pump.

At step 508, a model of a relationship between the at least one measurable pump parameter, the at least one hemodynamic parameter, and a cardiac parameter is accessed. The model may be produced by a machine learning or neural network algorithm to estimate a cardiac parameter from the measured hemodynamic and pump parameters, for example by the neural network described in FIGS. 2 and 3, or by any available machine learning process. The model may be stored in a controller of the blood pump (for example in memory 106 of FIG. 1), or may be hosted in a server or processor coupled to the blood pump controller or another processor which receives the measured parameters from a blood pump controller. At step 510, the model is used to estimate a cardiac parameter for the patient in the second patient set, based on the pump parameter measurement and the hemodynamic parameter measurement in the patient. The cardiac parameter may be a left ventricular volume, cardiac output, cardiac power output, compliance, native flow, stroke volume, volume at diastole or systole, or other relevant cardiac parameter, or any combination of the foregoing. The cardiac parameter of the patient is not otherwise measured so that no additional catheters or diagnostic devices need be inserted into the patient's vasculature. The estimated cardiac parameter can be used to inform health decisions made by a healthcare professional, and may be displayed to the healthcare professional, and/or used to recommend changes in support provided by the blood pump to the healthcare professional.

Figure 6:
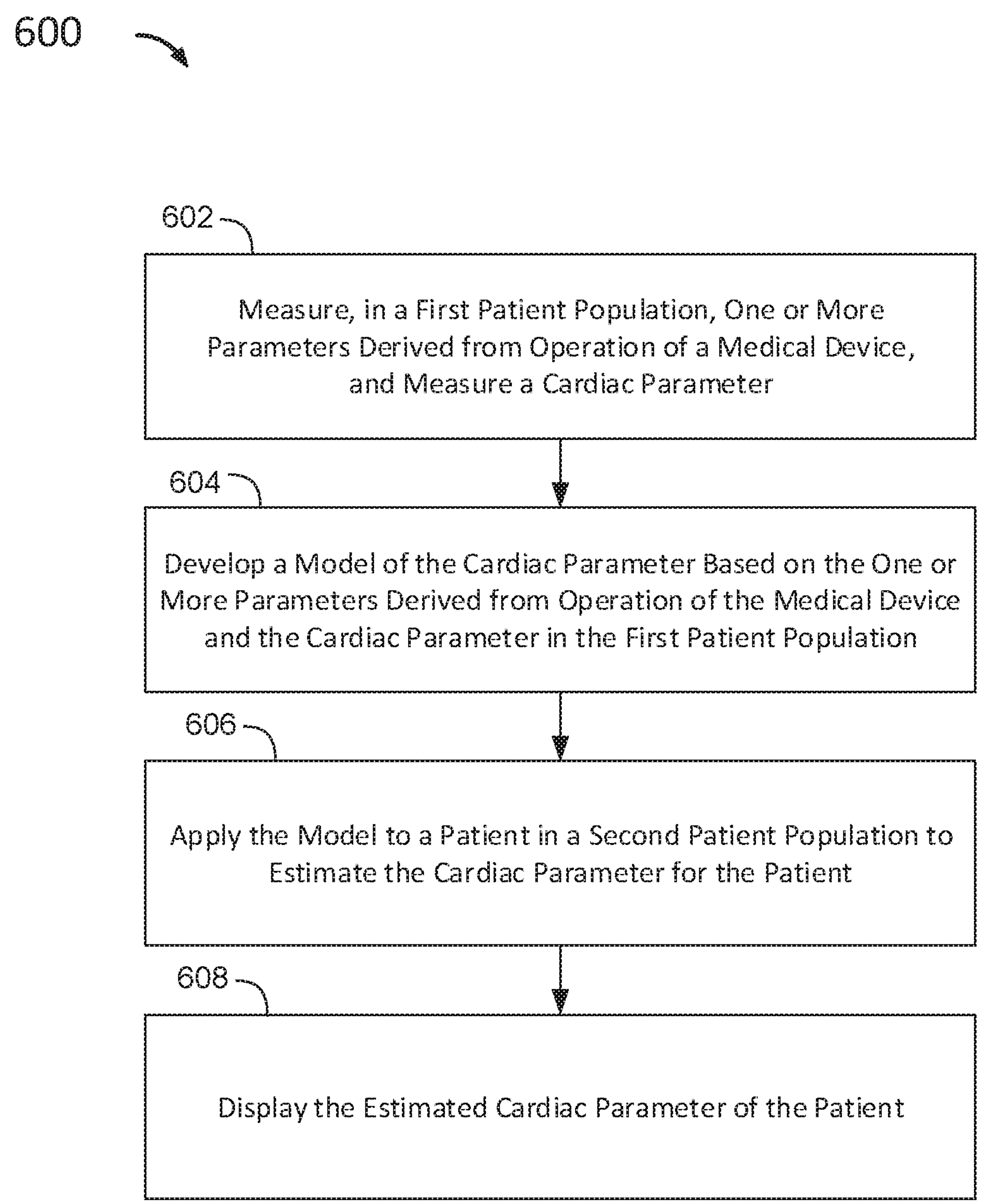
FIG. 6 shows a method for developing an estimate of a cardiac parameter in a patient.

FIG. 6 shows a method 600 for developing an estimate of a cardiac parameter in a patient. At step 602, one or more parameters derived from operation of a medical device and a cardiac parameter is measured in a first patient population. At step 604, a model of the cardiac parameter is developed based on the one or more parameters derived from operation of the medical device and the measured cardiac parameter in the first patient population. The model may be developed through use of machine learning or neural networks, such as those described in FIGS. 2 and 3, or by any other available machine learning process. At step 606, the model is applied to a patient in a second patient population to estimate the cardiac parameter in the patient. The cardiac parameter need not otherwise be determined in the patient.

At step 608, the estimated cardiac parameter of the patient is displayed, for example on a display associated with a medical device such as a blood pump. A healthcare professional may use the displayed estimated cardiac parameter to make healthcare decisions related to treatment and use of the medical device.

The model can be used to provide health care professionals with a continuous or nearly continuous estimate of a cardiac parameter while the medical device, such as a blood pump, is in the patient, enabling the health care professional to make real-time decisions about the patient's care. For example, where a blood pump is used in the patient, the provided estimated cardiac parameter can be used by a health care professional in decisions related to cardiac health, weaning the patient from the pumping device support or increasing support. The cardiac parameter may be a left ventricular volume, cardiac output, cardiac power output, compliance, native flow, stroke volume, volume at diastole or systole, or other relevant cardiac parameter, or any combination of the foregoing. Other hemodynamic or cardiac parameters may be extracted from the estimated cardiac parameter and provided to a health care professional as well.

In some embodiments, a controller of the blood pumping device may use the estimated cardiac parameter to determine a recommended course of action with regard to increased or decreased support by the blood pumping device. In particular, the controller can determine the recommended course of action based on a comparison of the estimated cardiac parameter with previous estimated cardiac parameters for the patient. In some embodiments, the controller may make a change to the support provided by the blood pumping device based on the proposed course of action.

FIGS. 7-9 illustrate exemplary graphs of parameters over time, comparing a model-predicted trace and a "true" trace obtained by direct measurement. As described above with regard to the FIGS. 4-6, models of cardiac parameters can be developed using the hemodynamic and pump or medical device data of a first patient population for use in a second patient population. The model of the cardiac parameter enables the estimation of the cardiac parameter in patients without requiring the use of additional diagnostic or sensing catheters in the vasculature of the patient which is safer and more efficient. Because well-developed algorithms may also take into account additional patient data such as sex, weight, disease state, and outcomes, the estimated cardiac parameter may be highly accurate. Further, the additional data taken into account in the development of the algorithm may be used to suggest treatment protocols or changes to the use or operation of the blood pump or other medical device to improve cardiac health of the patient based on the measured parameters and the application of the developed model. FIGS. 7-9 illustrate the accuracy of example models predicting cardiac parameters based on measured pump and hemodynamic parameters compared to the true measured cardiac parameter.

Figure 7A:
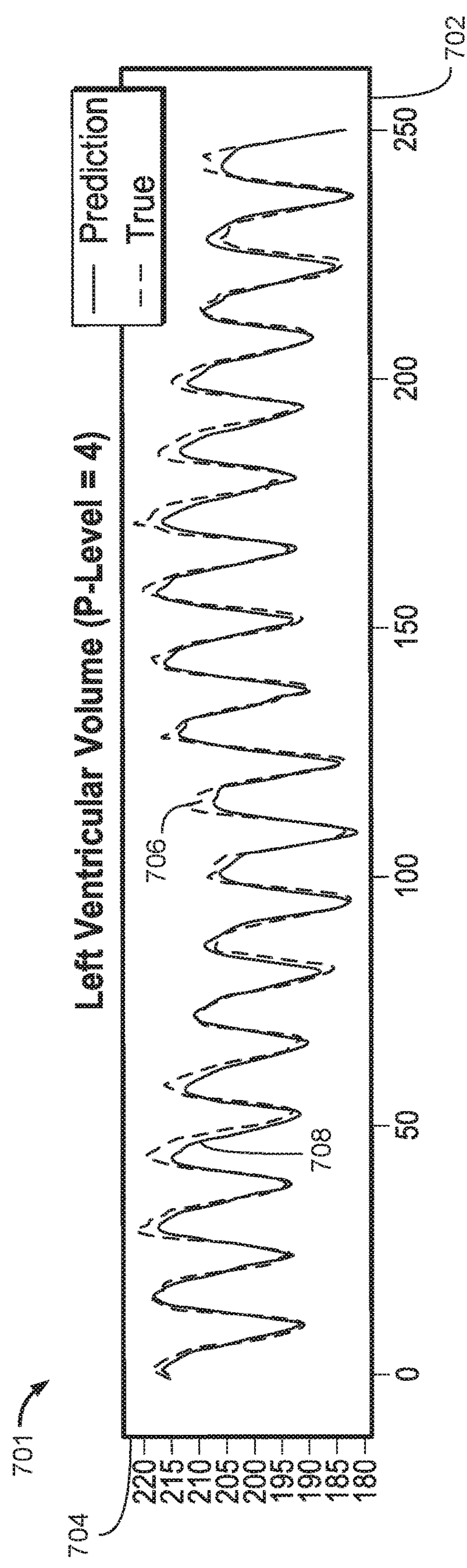
FIG. 7A shows an exemplary graph of measured left ventricular volume and predicted left ventricular volume based on an example relationship between an aortic pressure and pump flow.
Figure 7B:
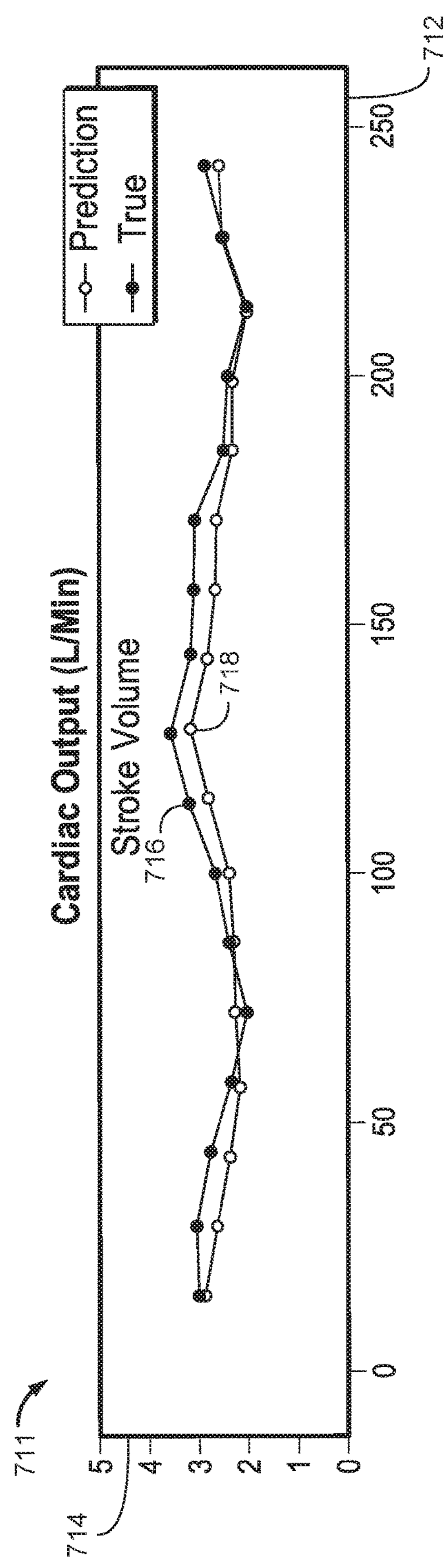
FIG. 7B shows an exemplary graph of measured cardiac output and predicted cardiac output based on an example relationship between an aortic pressure and pump flow.
Figure 7C:
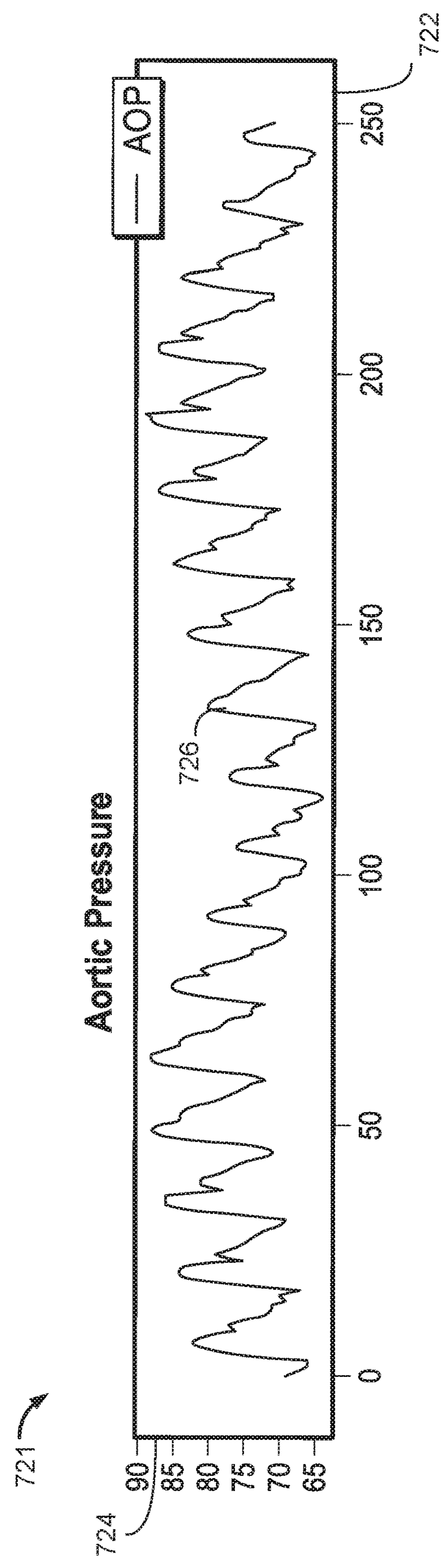
FIG. 7C shows an example measured aortic pressure used in the prediction of the left ventricular volume of FIG. 7A and the cardiac output of FIG. 7B.
Figure 7D:
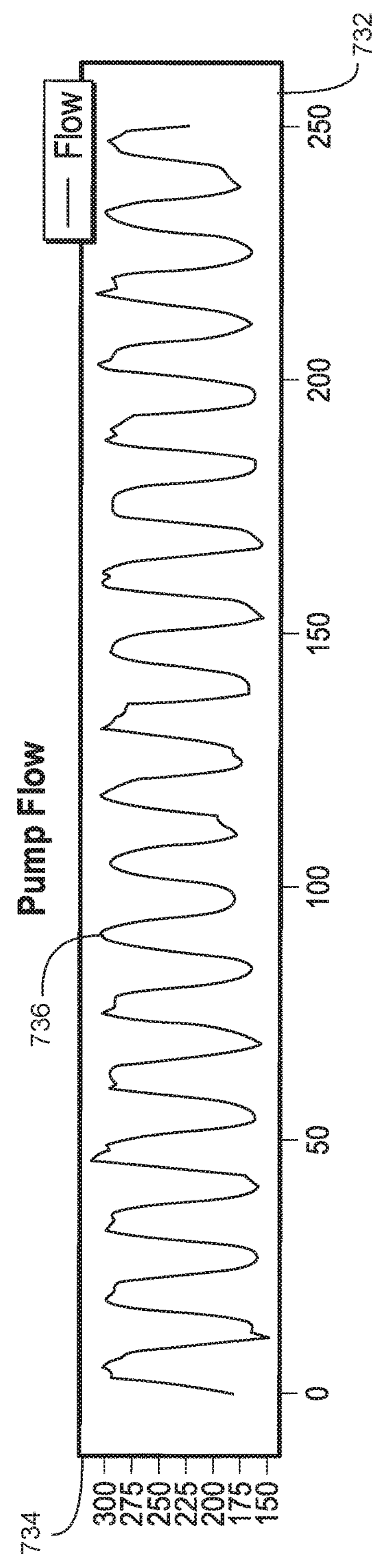
FIG. 7D shows an example measured pump flow used in the prediction of the left ventricular volume of FIG. 7A and the cardiac output of FIG. 7B.

FIGS. 7A-D shows exemplary graphs of various parameters over time during use of a particular blood pump operating at a pump power level ("P-level") of 4. FIG. 7A includes graph 701 showing the measured and estimated left ventricular volume at a particular pump power level (P-level=4). Graph 701 includes an x-axis 702 showing time in seconds, a y-axis 704 showing a volume in milliliters, a measured ("true") trace 706 of the measured left ventricular volume and an estimated ("prediction") trace 708 of the left ventricular volume as predicted by the example model based on the aortic pressure and pump flow as shown in FIGS. 7C and 7D.

FIG. 7B shows graph 711 showing the measured and estimated stroke volume of the pump. Graph 711 includes an x-axis 712 showing time in seconds, a y-axis 714 showing a stroke volume, a measured ("true") trace 716 of the measured stroke volume and an estimated ("prediction") trace 718 of the stroke volume as predicted by the example model based on the aortic pressure and pump flow as shown in FIGS. 7C and 7D. Stroke volume is related to cardiac output.

FIG. 7C shows graph 721 showing a trace of the measured aortic pressure over time for the pump, as used in the prediction of the left ventricular pressure in FIG. 7A and the stroke volume in FIG. 7B. Graph 721 includes an x-axis 722 showing time in seconds, a y-axis 724 showing an aortic pressure in mmHg, and a trace of the measured aortic pressure ("AoP").

FIG. 7D shows graph 731 showing a trace of the pump flow over time for the pump, as used in the prediction of the left ventricular pressure in FIG. 7A and the stroke volume in FIG. 7B. Graph 731 includes an x-axis 732 showing time in seconds, a y-axis 734 showing a flow rate in ml/s, and a trace of the measured flow rate. The x-axis for the four graphs in FIGS. 7A-D is the same.

FIGS. 7A-D illustrate that the example model accurately predicts the metrics of left ventricular volume and cardiac output based on the inputs of aortic pressure and flow rate for a pump operated at a constant pump power level.

Figure 8A:
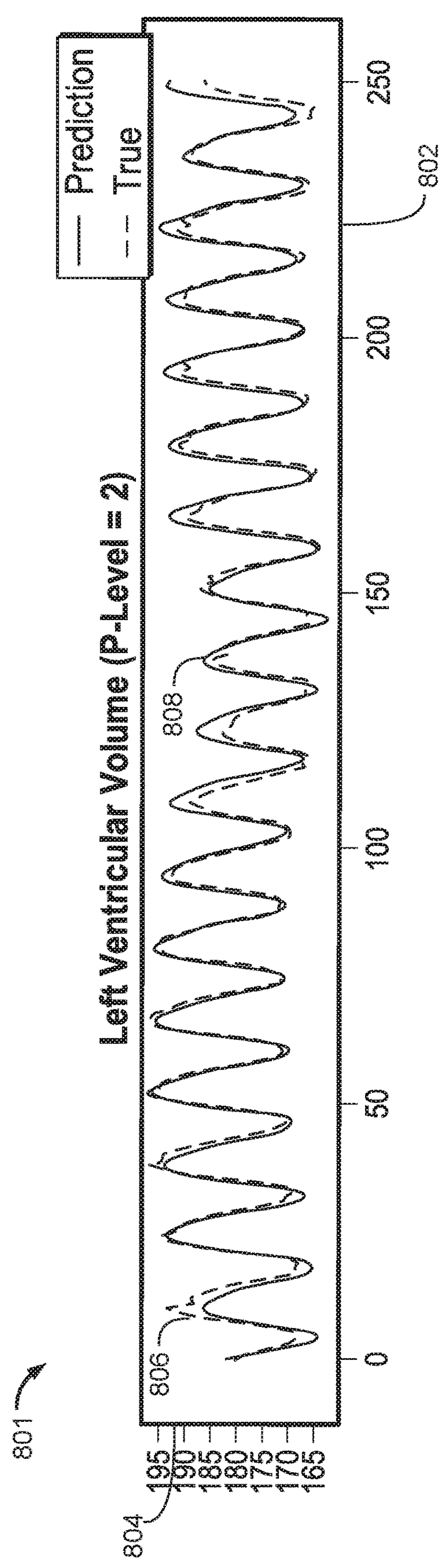
FIG. 8A shows an exemplary graph of measured left ventricular volume and predicted left ventricular volume based on an example relationship between an aortic pressure and pump flow and at a pump power level of 2.

FIGS. 8A-D shows exemplary graphs of both left ventricular volume and stroke volume at different pump power levels. FIG. 8A includes graph 801 showing the measured and estimated left ventricular volume at a particular pump power level of 2 (P-level=2). Graph 801 includes an x-axis 802 showing time in seconds, a y-axis 804 showing a volume in milliliters, a measured ("true") trace 806 of the measured left ventricular volume and an estimated ("prediction") trace 808 of the left ventricular volume as predicted by the example model for a pump operating at pump power level 2.

Figure 8B:
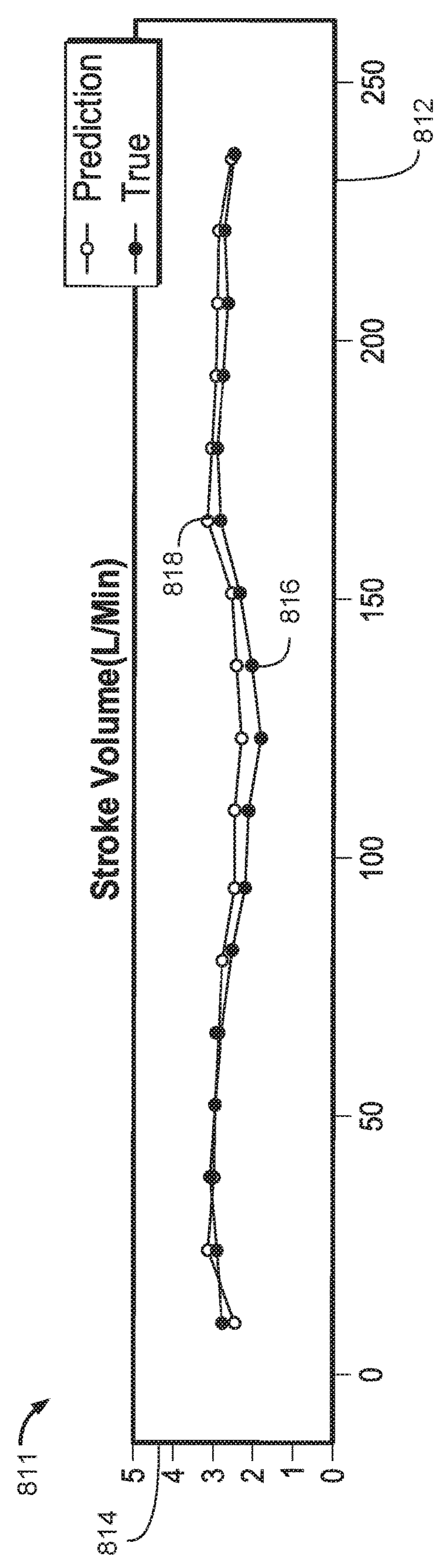
FIG. 8B shows an exemplary graph of measured stroke volume and predicted stroke volume based on an example relationship between an aortic pressure and pump flow and at a pump power level of 2.

FIG. 8B shows graph 811 showing the measured and estimated stroke volume of the pump at P-level=2. Graph 811 includes an x-axis 812 showing time in seconds, a y-axis 814 showing a stroke volume, a measured ("true") trace 816 of the measured stroke volume and an estimated ("prediction") trace 818 of the stroke volume as predicted by the example model for a pump operating at pump power level of 2.

Figure 8C:
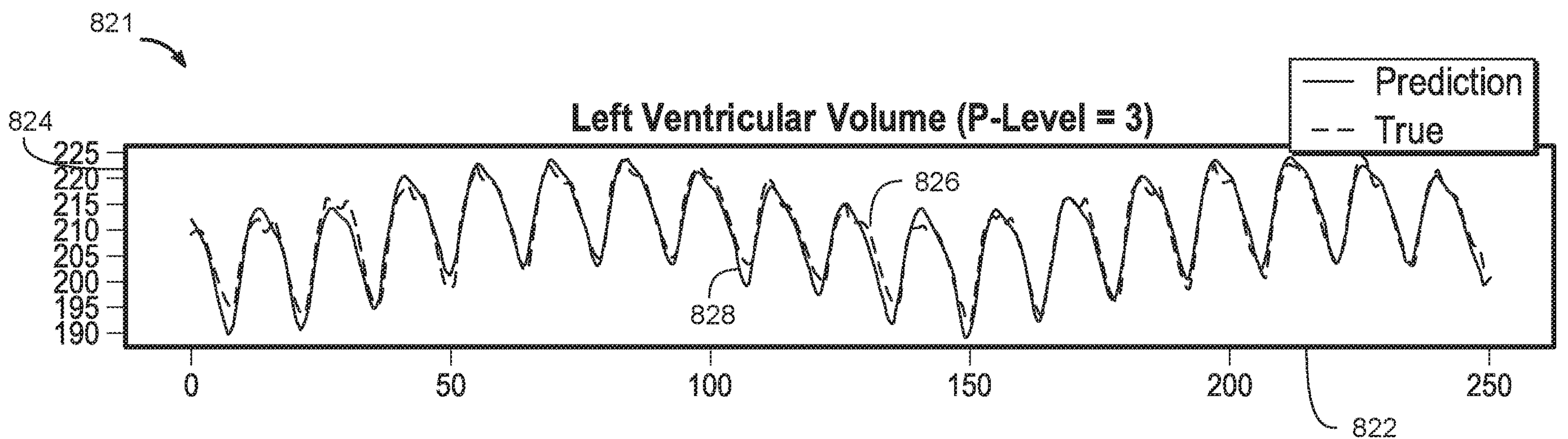
FIG. 8C shows an exemplary graph of measured left ventricular volume and predicted left ventricular volume based on an example relationship between an aortic pressure and pump flow and at a pump power level of 3.

FIG. 8C shows graph 821 showing measured and estimated left ventricular volume at pump power level of 3 (P-level=3). Graph 821 includes an x-axis 822 showing time in seconds, a y-axis 824 showing a volume in milliliters, a measured ("true") trace 826 of the measured left ventricular volume and an estimated ("prediction") trace 828 of the left ventricular volume as predicted by the example model for a pump operating at pump power level of 3.

Figure 8D:
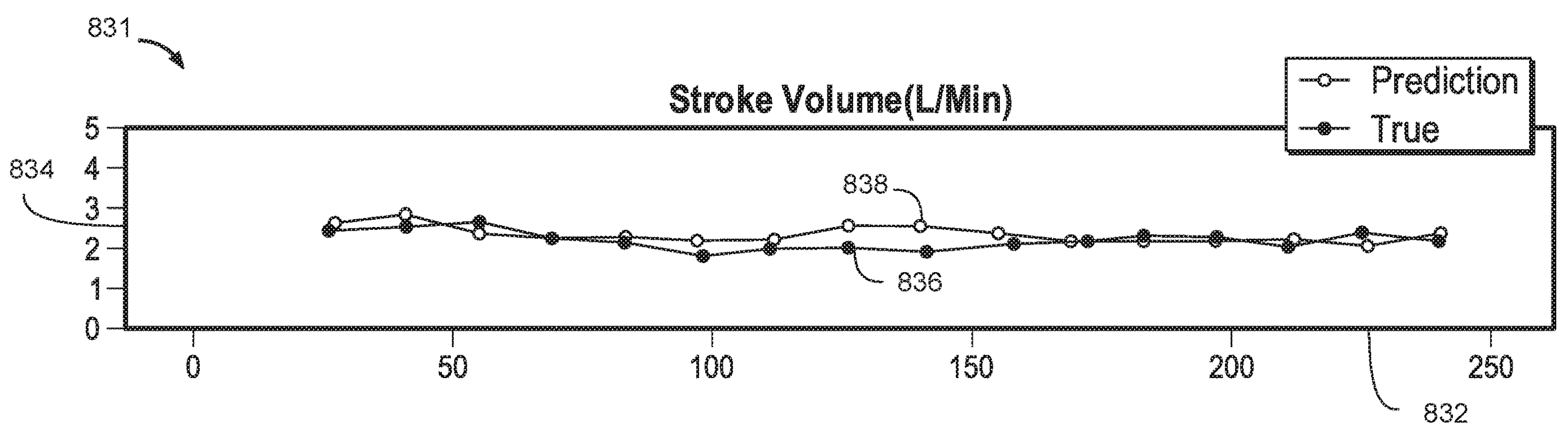
FIG. 8D shows an exemplary graph of measured stroke volume and predicted stroke volume based on an example relationship between an aortic pressure and pump flow and at a pump power level of 3.

FIG. 8D shows graph 831 showing the measured and estimated stroke volume of the pump at power level of 3. Graph 831 includes an x-axis 832 showing time in seconds, a y-axis 834 showing a stroke volume, a measured ("true") trace 836 of the measured stroke volume and an estimated ("prediction") trace 838 of the stroke volume as predicted by the example model for a pump operating at pump power level of 3. The x-axis for the four graphs in FIGS. 8A-D is the same, and the four graphs are all based on aortic pressure and pump flow rate as inputs to the model. FIGS. 8A-D illustrate that the example model is accurate at predicting the cardiac parameter even for blood pumps operating at various power levels.

Figure 9A:
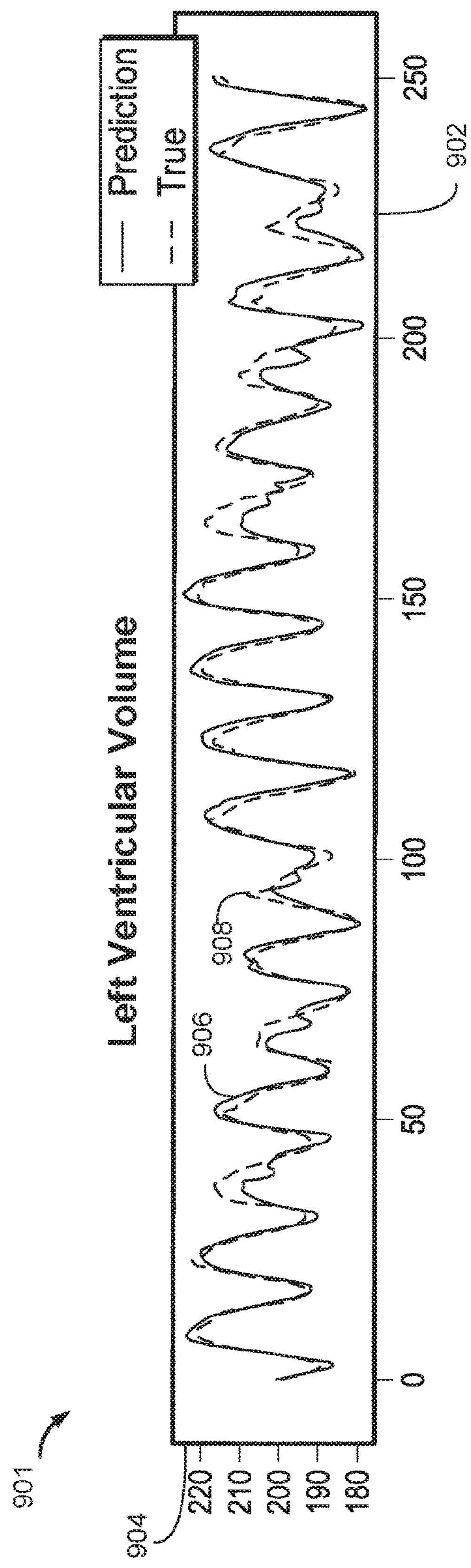
FIG. 9A shows an exemplary graph of measured left ventricular volume and predicted left ventricular volume based on an example relationship between an aortic pressure and pump flow for irregular waveforms.

FIGS. 9A-D show exemplary graphs of both left ventricular volume and stroke volume for irregular waveforms. FIG. 9A includes a graph 901 showing the measured and estimated left ventricular volume during occurrence of irregular waveforms in the heart. Graph 901 shows the measured and estimated left ventricular volume. Graph 901 includes an x-axis 902 showing time in seconds, a y-axis 904 showing a volume in milliliters, a measured ("true") trace 906 of the measured left ventricular volume and an estimated ("prediction") trace 908 of the left ventricular volume as predicted by the example model based on irregular waveforms.

Figure 9B:
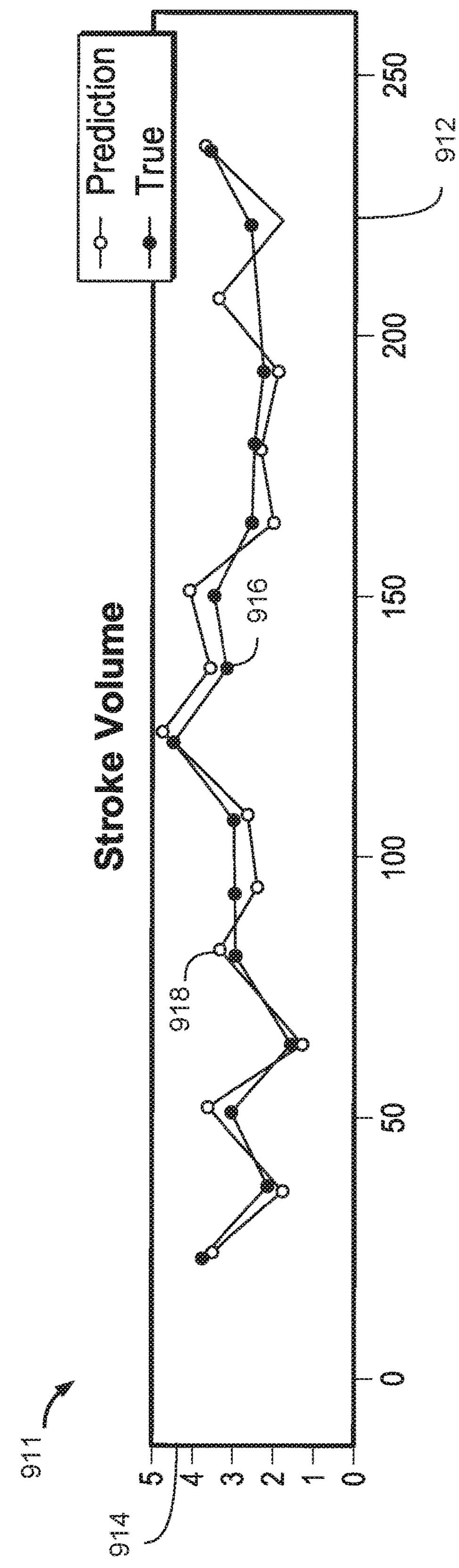
FIG. 9B shows an exemplary graph of measured stroke volume and predicted stroke volume based on an example relationship between an aortic pressure and pump flow for irregular waveforms.

FIG. 9B shows a graph 911 showing the measured and estimated stroke volume of the pump during occurrence of irregular waveforms in the heart. Graph 911 includes an x-axis 912 showing time in seconds, a y-axis 914 showing a stroke volume, a measured ("true") trace 916 of the measured stroke volume and an estimated ("prediction") trace 918 of the stroke volume as predicted by the example model based on irregular waveforms.

Figure 9C:
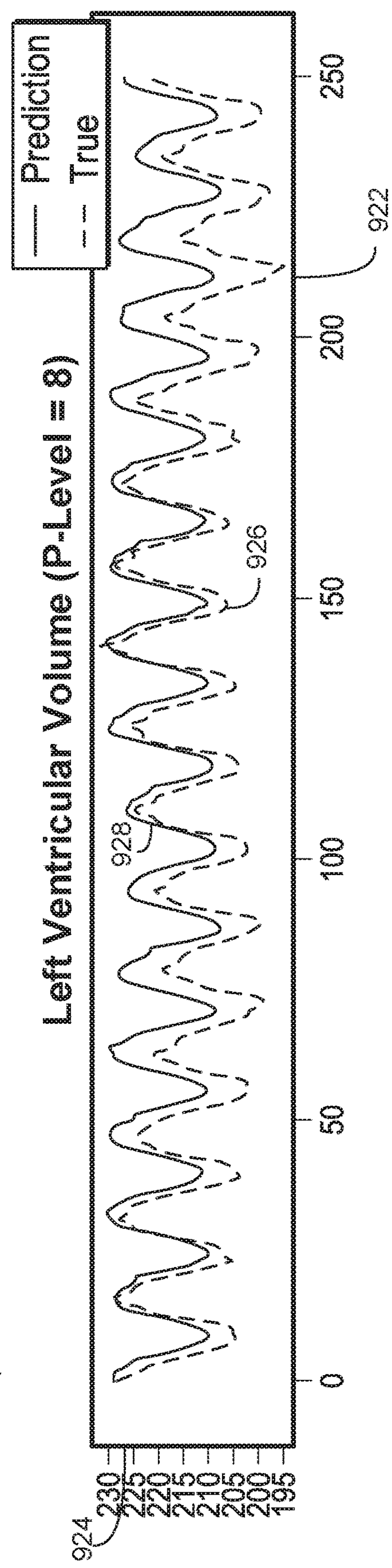
FIG. 9C shows an exemplary graph of measured left ventricular volume and predicted left ventricular volume based on an example relationship between an aortic pressure and pump flow for irregular waveforms.

FIG. 9C shows a third graph 921 showing measured and estimated left ventricular volume, during occurrence of irregular waveforms in the heart. FIG. 9C shows the predicted and true traces of the left ventricular volume during operation of a blood pump at pump power level 8 (P-level=8). Graph 921 includes an x-axis 922 showing time in seconds, a y-axis 924 showing a volume in milliliters, a measured ("true") trace 926 of the measured left ventricular volume and an estimated ("prediction") trace 928 of the left ventricular volume as predicted by the example model based on irregular waveforms.

Figure 9D:
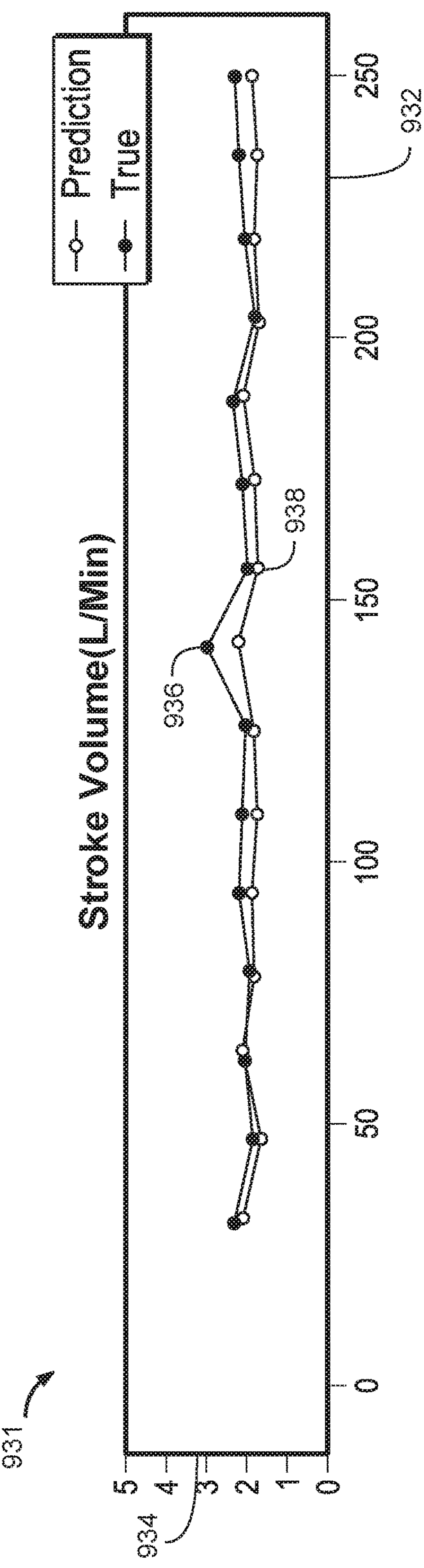
FIG. 9D shows an exemplary graph of measured stroke volume and predicted stroke volume based on an example relationship between an aortic pressure and pump flow for irregular waveforms.

FIG. 9D shows a fourth graph 931 showing the measured and estimated stroke volume during occurrence of irregular waveforms in the heart and during operation of a blood pump at P-level 8. Graph 931 includes an x-axis 932 showing time in seconds, a y-axis 834 showing a stroke volume, a measured ("true") trace 936 of the measured stroke volume and an estimated ("prediction") trace 938 of the stroke volume as predicted by the example model based on irregular waveforms. The x-axis for the four graphs of FIGS. 9A-D is the same, and the four graphs in FIGS. 9A-D are all based on aortic pressure and pump flow rate as inputs to the model. FIGS. 9A-D illustrates that even for irregular waveforms, the example model is accurate at predicting the cardiac parameter.

By creating a model relating blood pump parameters to a cardiac parameter based on a first patient population, and applying the model to a second patient population the cardiac parameter can be accurately estimated in the second patient population without the use of an additional measurement catheter or other diagnostic device. Estimating a cardiac parameter without the use of an additional device can be more efficient and also safer for some patients, as additional devices may take up additional space in the vasculature and/or interfere with the operation of cardiac support devices such as a blood pump. A machine learning algorithm can be used to construct a model of a measured cardiac parameter with one or more measurable parameters of a blood pump or other medical device based on data from a large number of patients having various characteristics. By taking into account a wide range of characteristics in the model, an accurate model can be developed which is helpful in predicting a cardiac parameter of a later patient. For example, characteristics such as sex, weight, disease state, cardiac outcomes, and diagnosis can be taken into account in the development of the model.

Various systems can be configured to carry out the steps of developing and applying the model as described above. For example, the model may be developed and/or implemented in a controller of a blood pump. For example, one or more models derived as described above may be stored in a memory of a controller. The controller may include one or more processors configured to drive and control a blood pump and to provide and/or receive information to a health care professional via a display. The one or more processors may access a model stored in the memory, receive blood pump parameter measurements as inputs from the blood pump, and extract, using the blood pump parameters, an estimated cardiac parameter from the model. The one or more processors may then display the estimated cardiac parameter as well as other health information on a display.

The model describes the cardiac parameter in terms of measurable pump parameters such as pump speed, flow, or pressure, and enables the details of pump function in the heart to be interpreted to understand the cardiac function of the heart without need for additional diagnostic tools such as additional catheters. The pump performance and the pressure signal measured at the blood pump can be used to estimate the cardiac output based on the model. This allows understanding and predicting of the left ventricular volume or other cardiac parameters of a patient based on pump parameters which are easily extracted from a blood pump device providing cardiac support.

The foregoing is merely illustrative of the principles of the disclosure, and the apparatuses can be practiced by other than the described implementations, which are presented for purposes of illustration and not of limitation. It is to be understood that the methods disclosed herein, while shown for use in automated ventricular assistance systems, may be applied to systems to be used in other automated medical systems.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

Embodiment A1: A method of estimating a cardiac parameter for a patient, the method comprising:

operating a blood pump within each patient in a first patient set, the blood pump having at least one measurable pump parameter;

measuring for each patient in the first patient set at least one hemodynamic parameter and the at least one measurable pump parameter to acquire a first hemodynamic parameter measurement and a first pump parameter measurement, building a model of a cardiac parameter based on a relationship between the at least one first hemodynamic parameter and the at least one measurable pump parameter for the first patient set, operating a second blood pump in a second patient in a second patient set; and applying the model to the second patient by:

measuring the at least one measurable pump parameter in the second patient to acquire a second pump parameter measurement;

measuring the at least one first hemodynamic parameter in the second patient to acquire a second hemodynamic parameter measurement; and estimating a cardiac parameter for the second patient, wherein the cardiac parameter for the second patient is output by the model based on the second pump parameter measurement and the second hemodynamic parameter measurement.

A2: The method of A1, wherein measuring at least one hemodynamic parameter comprises measuring the aortic pressure.

A3: The method of A1 or A2, the method further comprising determining the aortic pressure at a pressure sensor located on the blood pump.

A4: The method of any of A1-A3, wherein measuring the at least one measurable pump parameter comprises measuring pump flow.

A5: The method of any of A1-A4, the method further comprising determining an estimated cardiac parameter based on the at least one hemodynamic parameter and at least one measurable pump parameter for at least one time point.

A6: The method of any of A1-A5, the method further comprising inserting into each patient within the first patient set a sensing catheter separate from the blood pump.

A7: The method of any of A1-A6, the method further comprising measuring at the sensing catheter a measured cardiac parameter.

A8: The method of any of A1-A7, the method further comprising comparing the estimated cardiac parameter to the measured cardiac parameter.

A9: The method of any of A1-A8, wherein the sensing catheter is an inca catheter.

A10: The method of any of A1-A9, wherein the cardiac parameter is a left ventricular volume.

A11: The method of any of A1-A10, wherein the cardiac parameter is one of cardiac output, cardiac power output, stroke volume or compliance.

A12: The method of any of A1-A11, the method further comprising associating the model with patient information describing the first patient set.

A13: The method of any of A1-A12, wherein the patient information comprises a diagnosis or a demographic for each patient in the first set of patients.

A14: The method of any of A1-A13, wherein the diagnosis is one of cardiogenic shock or myocardial infarction.

A15: The method of any of A1-A14, wherein the demographic is one or more of sex, gender, risk factor, outcome, or age.

A16: The method of any of A1-A5, the method further comprising determining whether the model applies to the second patient based on the patient information associated with the model.

A17: The method of any of A1-A6, the method further comprising displaying the second pump parameter measurement and the second hemodynamic parameter measurement for the second patient on a display.

A18: The method of any of A1-A17, the method further comprising displaying the estimated cardiac parameter of the second patient on the display.

A19: The method of any of A1-A18, the method further comprising computing a suggested change in a pump speed based on the estimated cardiac parameter in the second patient.

A20: The method of any of A1-A19, the method further comprising implementing the suggested change in the pump speed.

A21: The method of any of A1-A20, the method further comprising displaying the suggested change in the pump speed on a display.

A22: The method of any of A1-A21, wherein building a model of a cardiac parameter comprises using a neural network to extract a model from the at least one first hemodynamic parameter and the at least one measurable pump parameter for the first patient set.

A23: The method of A22, wherein the neural network comprises a plurality of cells.

A24: The method of A23, wherein a first cell of the plurality of cells comprising the neural network accepts as inputs the at least one first hemodynamic parameter and the at least one measurable pump parameter for the first patient set at a first time point.

A25: The method of A24, wherein the first cell transforms the at least one first hemodynamic parameter and the at least one measurable pump parameter based on one or more model fits, before transmitting the transformed hemodynamic parameter and transformed pump parameter to a second cell of the plurality of cells.

A26: The method of A25, wherein the first cell updates a hidden state and a cell state for the first time point.

A27: The method of A26, wherein the first cell receives the at least one first hemodynamic parameter and the at least one measurable pump parameter for a second time point and updates the hidden state and the cell state for the second time point.

A28: The method of A22, wherein the neural network is a recurrent bi-directional neural network.

A29: The method of any of A1-A28, wherein the first patient set comprises one patient.

A30: The method of any of A1-A29, wherein a neural network is used to derive the model to be applied to input data.

A31: The method of A30, wherein the neural network comprises a plurality of cells which are in communication with one another and wherein the cells:

accept as inputs one or more measured parameters, transform the one or more measured parameters based on model fits, and transmit the transformed parameters to a neighboring cell with one or more of a hidden state and a cell state.

A32: A pump system having a controller configured to implement the method of any of A1-A31.

A33: A memory configured to carry out the method of any of A1-A31.

Embodiment B1: A method of estimating a cardiac parameter for a patient based on a model, the method comprising:

operating a blood pump in a patient;

measuring at least one measurable pump parameter of the blood pump in the patient to acquire a pump parameter measurement;

measuring at least one hemodynamic parameter in the patient to acquire a hemodynamic parameter measurement;

accessing from a database a model of a relationship between the at least one measurable pump parameter, the at least one hemodynamic parameter, and a cardiac parameter; and estimating a cardiac parameter estimate for the patient, wherein the cardiac parameter estimate for the patient is output by the model based on the pump parameter measurement and the hemodynamic parameter measurement.

B2: The method of B1, wherein measuring at least one hemodynamic parameter comprises measuring the aortic pressure.

B3: The method of B1 or B2, the method further comprising determining the aortic pressure at a pressure sensor located on the blood pump.

B4: The method of any of B1-B3, wherein measuring the at least one measurable pump parameter comprises measuring pump flow.

B5: The method of any of B1-B4, wherein the cardiac parameter is a left ventricular volume.

B6: The method of any of B1-B5, wherein the cardiac parameter is one of cardiac output, cardiac power output, stroke volume or compliance.

B7: The method of any of B1-B6, the method further comprising displaying the pump parameter measurement and the hemodynamic parameter measurement for the patient on a display.

B8: The method of any of B1-B7, the method further comprising displaying the cardiac parameter estimate of the patient on the display.

B9: The method of any of B1-B8, the method further comprising computing a suggested change in a pump speed based on the cardiac parameter estimated in the patient.

B10: The method of any of B1-B9, the method further comprising implementing the suggested change in the pump speed.

B11: The method of any of B1-B10, the method further comprising displaying the suggested change in the pump speed on a display.

B12: The method of any of B1-B11, wherein accessing a model comprises determining a selected model from a plurality of models.

B13: The method of any of B1-B12, wherein determining a selected model from a plurality of models comprises selecting a model based on information associated with the patient.

B14: The method of any of B1-B13, wherein accessing a model comprises choosing a model formed by a neural network.

B15: The method of B14, wherein the neural network is a recurrent bi-directional neural network.

B16: The method of any of B1-B15, further comprising determining a recommended change in the operation of the blood pump based on the estimated cardiac parameter.

B17: The method of any of B1-B16, wherein a neural network is used to derive the model to be applied to input data.

B18: The method of B17, wherein the neural network comprises a plurality of cells which are in communication with one another and wherein the cells:

accept as inputs one or more measured parameters, transform the one or more measured parameters based on model fits, and transmit the transformed parameters to a neighboring cell with one or more of a hidden state and a cell state.

B19: A pump system having a controller configured to implement the method of any of B1-B18.

B20: A memory configured to carry out the method of any of B1-B18.

Embodiment C1: A method for developing an estimate of a cardiac parameter in a patient, the method comprising:

measuring, in a first patient population, one or more parameters derived from operation of a medical device and measuring a cardiac parameter;

developing a model of the cardiac parameter based on the one or more parameters derived from operation of the medical device and the cardiac parameter in the first patient population;

applying the model to a patient in a second patient population to estimate the cardiac parameter for the patient.

C2: The method of C1, the method further comprising:

labeling the model according to common characteristics of one or more patients in the first patient population.

C3: The method of C1 or C2, the method further comprising:

determining, based on the labeling of the model, whether the model is applicable to the patient in the second patient population by comparing characteristics of the patient in the second patient population with the characteristics of the one or more patients in the first patient population.

C4: The method of any of C1-C3, wherein developing the model o further comprises:

utilizing a machine learning algorithm to develop a model of the cardiac parameter based on the one or more parameters derived from operation of the medical device and the measured cardiac parameter in the first patient population.

C5: The method of any of C1-C4, wherein applying the model to the patient in the second patient population further comprises:

operating the medical device in the patient in the second patient population;

measuring, in the patient in the second patient population, the one or more parameters derived from operation of the medical device;

inputting the measured one or more parameters derived from operation of the medical device into the model of the cardiac parameter; and estimating, based on the model, an estimated cardiac parameter of the patient in the second patient population.

C6: The method of any of C1-C5, wherein a neural network is used to derive the model to be applied to input data.

C7: The method of C6, wherein the neural network comprises a plurality of cells which are in communication with one another and wherein the cells:

accept as inputs one or more measured parameters, transform the one or more measured parameters based on model fits, and transmit the transformed parameters to a neighboring cell with one or more of a hidden state and a cell state.

C8: A pump system having a controller configured to implement the method of any of C1-C7.

C9: A memory configured to carry out the method of any of C1-C7.

Embodiment D1: A system for estimating a cardiac parameter of a patient based on a pre-determined model, the system comprising:

a blood pump comprising:

a drivable rotor, the rotor configured to be driven at one or more pump speeds; and a sensor configured to measure a hemodynamic parameter; and a controller comprising:

a memory configured to receive a hemodynamic parameter measurement from the sensor and record the hemodynamic parameter measurement, the memory also storing a pre-determined model of a cardiac parameter based on the hemodynamic parameter and a pump speed of the one or more pump speeds;

a driver configured to drive the rotor, the driver configured to transmit a pump speed of the driven blood pump rotor to the memory to be recorded;

a display configured to display one or more parameters recorded in the memory;

wherein the memory is configured to:

determine from the pre-determined model, based on the hemodynamic parameter measurement and the pump speed, an associated cardiac parameter, and transmit the determined cardiac parameter to the display.

D2: The system of D1, wherein the memory is configured to store a plurality of pre-determined models of the cardiac parameter based on the hemodynamic parameter and the pump speed.

D3: The system of D2 wherein the controller is configured to select one pre-determined model from the plurality of stored pre-determined models based on at least one of the hemodynamic parameter and the pump speed.

D4: The system of D2, wherein the controller is configured to select one pre-determined model from the plurality of stored pre-determined models based on an input to the display.

D5: The system of any of D2-D3, wherein the plurality of pre-determined models are formed by a neural network which comprises a plurality of cells.

D6: The system of D5, wherein the neural network is a recurrent bi-directional neural network.

D7: The system of any of D1-D6, wherein the memory is configured to connect wirelessly to a database containing a plurality of pre-determined models of the cardiac parameter based on the hemodynamic parameter and the pump speed.

D8: The system D7, wherein the controller is configured to select one pre-determined model from the database and retrieve the selected one pre-determined model for storage in the memory.

D9: The system of claim D7 or D8, wherein the plurality of pre-determined models are formed by a neural network which comprises a plurality of cells.

D10: The system of any of D5-D9, wherein the neural network is a recurrent bi-directional neural network.

D11: The system of any of D1-D10, wherein the controller is configured to determine a recommended change to the pump speed based on the determined cardiac parameter.

D12: The system of D11, wherein the controller is further configured to generate for display on the display the recommended change to the pump speed.

D13: The system of D11 or D12, wherein the controller is configured to implement the recommended change to the pump speed.

D14: The system of any of D1-D13, wherein the sensor is configured to measure at least one of aortic pressure, left ventricular end diastolic pressure, and capillary wedge pressure.

D15: The system of any of D1-D14, wherein the cardiac parameter is left ventricular volume.

D16: The system of any of D1-D14, wherein the cardiac parameter is cardiac power output.

D17: The method of any of D1-D16, wherein a neural network is used to derive the model to be applied to input data.

D18: The method of D17, wherein the neural network comprises a plurality of cells which are in communication with one another and wherein the cells:

accept as inputs one or more measured parameters, transform the one or more measured parameters based on model fits, and transmit the transformed parameters to a neighboring cell with one or more of a hidden state and a cell state.

D19: A pump system having a controller configured to implement the method of any of D1-D18.

D20: A memory configured to carry out the method of any of D1-D18.

Embodiment E1: A method of estimating a cardiac parameter for a patient using a database, the method comprising:

operating a blood pump in a first patient;

measuring at least one measurable pump parameter of the blood pump in the first patient to acquire a pump parameter measurement;

measuring at least one hemodynamic parameter in the first patient to acquire a hemodynamic parameter measurement;

accessing a database comprising patient data for patients other than the first patient, wherein the patient data includes at least one of a measurable pump parameter, a hemodynamic parameter, and a cardiac parameter; and based on the pump parameter measurement in the first patient, hemodynamic parameter measurement in the first patient, and stored patient data from the database, estimating a cardiac parameter for the first patient.

E2: The method of E1, wherein the cardiac parameter is cardiac power output.

E3: The method of E1 or E2, wherein the database is a global database storing data from patients having different characteristics, and different medical conditions.

E4: The method of any of E1-E3, wherein characteristics include age, weight, sex, or BMI.

E5: The method of any of E1-E4, wherein the database is periodically updated with new data.

E6: The method of any of E1-E5, wherein a neural network is used to derive the model to be applied to input data.

E7: The method of E6, wherein the neural network comprises a plurality of cells which are in communication with one another and wherein the cells:

accept as inputs one or more measured parameters, transform the one or more measured parameters based on model fits, and transmit the transformed parameters to a neighboring cell with one or more of a hidden state and a cell state.

E8: A pump system having a controller configured to implement the method of any of E1-E7.

E9: A memory configured to carry out the method of any of E1-E7.

What is claimed:

1. A method of estimating a cardiac parameter for a patient, the method comprising:

obtaining patient data for a first set of patients, wherein the patient data comprises measurements of at least one blood pump parameter for each patient in the first set of patients and measurements of at least one hemodynamic parameter for each patient in the first set of patients;

building, with a neural network, a model of a cardiac parameter based on the patient data, wherein the neural network communicates over time in hidden states, and wherein the neural network iteratively develops the model based on a plurality of activation functions;

operating a blood pump in a second patient in a second set of patients; and applying the model to the second patient by:

measuring the at least one blood pump parameter in the second patient to acquire a blood pump parameter measurement;

measuring the at least one hemodynamic parameter in the second patient to acquire a hemodynamic parameter measurement; and estimating a cardiac parameter for the second patient, wherein the cardiac parameter for the second patient is output by the model based on the blood pump parameter measurement for the second patient and the hemodynamic parameter measurement for the second patient.

2. The method of claim 1, wherein each one of the measurements of the at least one hemodynamic parameter for the first set of patients is obtained with a respective sensing catheter separate from a respective blood pump.

3. The method of claim 1, further comprising associating the model with patient information describing the first patient set, wherein the patient information comprises a diagnosis or a demographic for each patient in the first set of patients.

4. The method of claim 3, further comprising determining whether the model applies to the second patient based on the patient information associated with the model.

5. The method of claim 1, further comprising computing a suggested change in a pump speed based on the estimated cardiac parameter for the second patient.

6. The method of claim 5, further comprising implementing the suggested change in the pump speed.

7. The method of claim 1, wherein the neural network comprises a plurality of cells, and wherein a first cell of the plurality of cells accepts as inputs the measurements of the at least one hemodynamic parameter and the measurements of the at least one blood pump parameter for the first set of patients at a first time point.

8. The method of claim 7, wherein the first cell transforms the measurements of the at least one hemodynamic parameter and the measurements of the at least one blood pump parameter based on one or more model fits, before transmitting the transformed measurements of the at least one hemodynamic parameter and the transformed measurements of the at least one blood pump parameter to a second cell of the plurality of cells.

9. The method of claim 1, wherein the at least one hemodynamic parameter is an aortic pressure, and wherein the at least one blood pump parameter is a pump flow.

10. The method of claim 9, wherein the cardiac parameter is one of a cardiac output, a cardiac power output, a stroke volume, or a compliance.

11. The method of claim 1, wherein the neural network is a stacked bi-directional recurrent neural network.

12. The method of claim 1, wherein the neural network has three or more levels of cells stacked between an input row and an output row.

13. The method of claim 1, wherein the neural network is a fully recurrent neural network, an Elman network, a Hopfield network, an Echo state network, or a hierarchical neural network.

14. The method of claim 1, wherein the plurality of activation functions comprises a sigmoidal function.

15. The method of claim 1, wherein the plurality of activation functions comprises a hyperbolic tangent function.

16. The method of claim 1, wherein the plurality of activation functions comprises a sigmoidal function and a hyperbolic tangent function.

17. A system for estimating a cardiac parameter of a patient based on a pre-determined model, the system comprising:

a blood pump comprising:

a rotor configured to be driven at one or more pump speeds; and a sensor configured to measure a hemodynamic parameter; and a controller comprising:

a driver configured to drive the rotor;

a display configured to display one or more parameters; and a non-transitory computer readable storage medium storing:

a pre-determined model of a cardiac parameter, wherein the pre-determined model is formed by a neural network based on patient data for a first set of patients, wherein the patient data comprises measurements of at least one blood pump parameter for each patient in the first set of patients and measurements of at least one hemodynamic parameter for each patient in the first set of patients, wherein the neural network communicates over time in hidden states, and wherein the neural network iteratively develops the pre-determined model based on a plurality of activation functions; and instructions that, when executed by one or more processors, cause the one or more processors to:

receive a hemodynamic parameter measurement for a second patient in a second set of patients from the sensor and record the hemodynamic parameter measurement;

receive a pump speed of the driven blood pump rotor from the driver and record the pump speed;

determine from the pre-determined model, based on the hemodynamic parameter measurement and the pump speed, an associated cardiac parameter; and transmit the determined cardiac parameter to the display.

18. The system of claim 17, wherein the instructions further cause the one or more processors to:

determine a recommended change to the pump speed based on the determined cardiac parameter; and transmit the recommended change to the pump speed to the display.

19. The system of claim 17, wherein the sensor is configured to measure at least one of aortic pressure, left ventricular end diastolic pressure, and capillary wedge pressure.

20. The system of claim 17, wherein the plurality of activation functions comprises a sigmoidal function and a hyperbolic tangent function.

* * * * *

UNITED STATES PATENT AND TRADEMARK OFFICE

CERTIFICATE OF CORRECTION

PATENT NO. : 11,694,813 B2
APPLICATION NO. : 16/743797
DATED : July 4, 2023
INVENTOR(S) : El Katerji et al.

It is certified that error appears in the above-identified patent and that said Letters Patent is hereby corrected as shown below:

In the Specification

Column 9, Detailed Description, Line 59, Delete “107” and insert --106-- therefor;

Column 10, Detailed Description, Line 60, Delete “226” and insert --222-- therefor.

Signed and Sealed this
Twelfth Day of September, 2023

Katherine Kelly Vidal

Katherine Kelly Vidal
*Director of the United States Patent and Trademark Office*